(12) United States Patent
Lawrence et al.

(10) Patent No.: US 10,950,149 B2
(45) Date of Patent: Mar. 16, 2021

(54) DISPENSING DEVICE

(71) Applicant: TRUDELL MEDICAL INTERNATIONAL, London (CA)

(72) Inventors: Greg Lawrence, London (CA); Peter M. Scarrott, London (CA)

(73) Assignee: Trudell Medical International

( * ) Notice: Subject to any disclaimer, the term of this patent is extended or adjusted under 35 U.S.C. 154(b) by 1274 days.

(21) Appl. No.: 15/014,424

(22) Filed: Feb. 3, 2016

(65) Prior Publication Data

US 2016/0217717 A1 Jul. 28, 2016

Related U.S. Application Data

(63) Continuation of application No. 13/414,411, filed on Mar. 7, 2012, now Pat. No. 9,265,901, which is a continuation of application No. 11/888,308, filed on Jul. 31, 2007, now Pat. No. 8,141,550.

(60) Provisional application No. 60/834,764, filed on Aug. 1, 2006.

(51) Int. Cl.
*G09F 11/04* (2006.01)
*A61M 15/00* (2006.01)

(52) U.S. Cl.
CPC .......... *G09F 11/04* (2013.01); *A61M 15/009* (2013.01); *A61M 15/0076* (2014.02); *A61M 15/0081* (2014.02); *A61M 15/0086* (2013.01)

(58) Field of Classification Search
None
See application file for complete search history.

(56) References Cited

U.S. PATENT DOCUMENTS

| | | | |
|---|---|---|---|
| 165,054 | A | 6/1875 | Baldwin |
| 498,851 | A | 6/1893 | Jones |
| 1,219,858 | A | 3/1917 | Patterson |
| 2,455,962 | A | 12/1948 | Wheeler et al. |
| 2,580,292 | A | 12/1951 | Geary et al. |
| 2,587,147 | A | 2/1952 | Guion et al. |
| 2,630,027 | A | 3/1953 | Wunderlich |
| 2,644,452 | A | 7/1953 | Brown |
| 2,767,680 | A | 10/1956 | Lermer |
| 2,770,711 | A | 11/1956 | Baranowski |
| 2,841,190 | A | 7/1958 | Scheck |

(Continued)

FOREIGN PATENT DOCUMENTS

| | | |
|---|---|---|
| AU | 598250 B2 | 6/1990 |
| CA | 535518 | 1/1957 |

(Continued)

OTHER PUBLICATIONS

International Search Report in International Application No. PCT/IB03/01032, dated Aug. 19, 2003, 10 pages.

(Continued)

*Primary Examiner* — Rachel T Sippel
(74) *Attorney, Agent, or Firm* — Brinks Gilson & Lione

(57) ABSTRACT

A dispenser includes a dispenser housing, an indicating device connected to the dispenser housing and a container removably engaged with the dispenser housing. The container and the dispenser housing remain connected as the container is moved between an engaged position and a disengaged position relative to the dispenser housing. The dispenser housing includes an upper portion pivotally connected to a lower portion.

28 Claims, 32 Drawing Sheets

(56) References Cited

U.S. PATENT DOCUMENTS

| | | |
|---|---|---|
| 2,883,086 A | 4/1959 | Davison et al. |
| 2,939,597 A | 6/1960 | Greene |
| 2,943,730 A | 7/1960 | Tregilgas |
| 2,953,242 A | 9/1960 | Shaw |
| 3,001,524 A | 9/1961 | Maison et al. |
| 3,073,468 A | 1/1963 | Arneson |
| 3,085,745 A | 4/1963 | Auberger |
| 3,119,557 A | 1/1964 | Chapman |
| 3,120,318 A | 2/1964 | Rigor |
| 3,148,801 A | 9/1964 | Radeloff et al. |
| 3,151,599 A | 10/1964 | Livingston |
| 3,170,597 A | 2/1965 | Reichenberger |
| 3,187,963 A | 6/1965 | Anderson |
| 3,189,232 A | 6/1965 | Joffe |
| 3,191,867 A | 6/1965 | Helms |
| 3,240,389 A | 3/1966 | Genua |
| 3,334,731 A | 8/1967 | Dale |
| 3,344,951 A | 10/1967 | Gervais |
| 3,361,306 A | 1/1968 | Grim |
| 3,402,863 A | 9/1968 | Green |
| 3,419,187 A | 12/1968 | Bazarnic |
| 3,446,179 A | 5/1969 | Bender |
| 3,477,561 A | 11/1969 | Espinal |
| 3,495,567 A | 2/1970 | Hayes et al. |
| 3,511,409 A | 5/1970 | Huck |
| 3,549,057 A | 12/1970 | Perez |
| 3,568,629 A | 3/1971 | Porter |
| 3,572,282 A | 3/1971 | Trump et al. |
| 3,589,563 A | 6/1971 | Carragan et al. |
| 3,612,349 A | 10/1971 | Thomas |
| 3,654,890 A | 4/1972 | Rigney et al. |
| 3,655,952 A | 4/1972 | Johnson et al. |
| 3,688,945 A | 9/1972 | Harman, Jr. et al. |
| 3,753,417 A | 8/1973 | Garby |
| 3,766,882 A | 10/1973 | Babbitt, III |
| 3,789,843 A | 2/1974 | Armstrong et al. |
| 3,792,242 A | 2/1974 | Hanson |
| 3,796,348 A | 3/1974 | Zipper |
| 3,797,748 A | 3/1974 | Nozawa et al. |
| 3,802,608 A | 4/1974 | Gullett |
| 3,831,808 A | 8/1974 | Bender |
| 3,831,812 A | 8/1974 | Dolan |
| 3,845,883 A | 11/1974 | Johnson et al. |
| 3,848,774 A | 11/1974 | Schimke |
| 3,886,879 A | 6/1975 | Frost et al. |
| 3,887,099 A | 6/1975 | Gillman et al. |
| 3,921,568 A | 11/1975 | Fish |
| 3,926,326 A | 12/1975 | Grau |
| 3,950,939 A | 4/1976 | Meisner |
| 3,960,713 A | 6/1976 | Carey |
| 3,977,554 A | 8/1976 | Costa |
| 3,994,421 A | 11/1976 | Hansen |
| 4,011,829 A | 3/1977 | Wachsmann et al. |
| 4,029,033 A | 6/1977 | Kerwin et al. |
| 4,034,757 A | 7/1977 | Glover |
| 4,037,719 A | 7/1977 | Perlmutter |
| 4,069,935 A | 1/1978 | Hampel |
| 4,069,942 A | 1/1978 | Marshall et al. |
| 4,074,831 A | 2/1978 | Roach |
| 4,078,661 A | 3/1978 | Thomas |
| 4,094,408 A | 6/1978 | Ford |
| 4,162,746 A | 7/1979 | Anderson et al. |
| 4,164,301 A | 8/1979 | Thayer |
| 4,188,984 A | 2/1980 | Lyall |
| 4,220,247 A | 9/1980 | Kramer |
| 4,291,688 A | 9/1981 | Kistler |
| 4,300,548 A | 11/1981 | Jones |
| 4,319,128 A | 3/1982 | Dow et al. |
| 4,345,541 A | 8/1982 | Villa-Real |
| 4,347,804 A | 9/1982 | Villa-Real |
| 4,347,853 A | 9/1982 | Gereg et al. |
| 4,350,265 A | 9/1982 | Griffiths et al. |
| 4,354,621 A | 10/1982 | Knickerbocker |
| 4,357,192 A | 11/1982 | Moser |
| 4,365,722 A | 12/1982 | Kramer |
| 4,368,381 A | 1/1983 | Ishiyama |
| 4,405,045 A | 9/1983 | Villa-Real |
| 4,419,016 A | 12/1983 | Zoltan |
| 4,432,300 A | 2/1984 | Lyss |
| 4,436,223 A | 3/1984 | Wilson |
| 4,440,306 A | 4/1984 | Van Buskirk et al. |
| 4,489,834 A | 12/1984 | Thackrey |
| 4,500,005 A | 2/1985 | Forrester |
| 4,501,370 A | 2/1985 | Kelley |
| 4,509,515 A | 4/1985 | Altounyan et al. |
| 4,511,150 A | 4/1985 | Seguenot |
| 4,523,933 A | 6/1985 | Laush et al. |
| 4,528,933 A | 7/1985 | Allen |
| 4,534,345 A | 8/1985 | Wetterlin |
| 4,538,744 A | 9/1985 | Weissenborn |
| 4,548,157 A | 10/1985 | Hevoyan |
| 4,562,933 A | 1/1986 | Dennis |
| 4,565,302 A | 1/1986 | Pfeiffer et al. |
| 4,599,508 A | 7/1986 | Smetaniuk |
| 4,634,012 A | 1/1987 | Kelley |
| 4,637,528 A | 1/1987 | Wachinski et al. |
| 4,641,759 A | 2/1987 | Kelley |
| 4,646,936 A | 3/1987 | Frazier et al. |
| 4,662,520 A | 5/1987 | Griffin |
| 4,664,107 A | 5/1987 | Wass |
| 4,666,051 A | 5/1987 | Trick |
| 4,668,218 A | 5/1987 | Virtanen |
| 4,677,975 A | 7/1987 | Edgar et al. |
| 4,693,399 A | 9/1987 | Hickman et al. |
| 4,705,182 A | 11/1987 | Newell-Lewis |
| 4,722,729 A | 2/1988 | Dettbarn et al. |
| 4,723,673 A | 2/1988 | Tartaglia et al. |
| 4,727,886 A | 3/1988 | Conrardy et al. |
| 4,736,871 A | 4/1988 | Luciani et al. |
| 4,749,093 A | 6/1988 | Trick |
| 4,753,189 A | 6/1988 | Mastman et al. |
| 4,756,423 A | 7/1988 | Holtsch |
| 4,782,966 A | 11/1988 | Thackrey |
| 4,792,664 A | 12/1988 | Schwab |
| 4,817,822 A | 4/1989 | Rand et al. |
| 4,890,572 A | 1/1990 | Huang |
| 4,896,855 A | 1/1990 | Furnish |
| 4,934,358 A | 6/1990 | Nilsson et al. |
| 4,934,568 A | 6/1990 | Fuchs |
| 4,947,875 A | 8/1990 | Brooks et al. |
| 4,955,371 A | 9/1990 | Zamba et al. |
| 4,969,578 A | 11/1990 | Gander et al. |
| 4,973,250 A | 11/1990 | Milman |
| 4,984,158 A | 1/1991 | Hillsman |
| 5,009,338 A | 4/1991 | Barker |
| 5,011,032 A | 4/1991 | Rollman |
| 5,020,527 A | 6/1991 | Dessertine |
| 5,027,806 A | 7/1991 | Zoltan et al. |
| 5,027,808 A | 7/1991 | Rich et al. |
| 5,038,972 A | 8/1991 | Muderlak et al. |
| 5,060,643 A | 10/1991 | Rich et al. |
| 5,069,204 A | 12/1991 | Smith et al. |
| 5,082,129 A | 1/1992 | Kramer |
| 5,082,130 A | 1/1992 | Weinstein |
| 5,115,929 A | 5/1992 | Buono |
| 5,174,473 A | 12/1992 | Marelli |
| 5,184,761 A | 2/1993 | Lee |
| 5,188,251 A | 2/1993 | Kusz |
| 5,190,643 A | 3/1993 | Duncan et al. |
| 5,209,375 A | 5/1993 | Fuchs |
| 5,215,079 A | 6/1993 | Fine et al. |
| 5,217,004 A | 6/1993 | Blasnik et al. |
| 5,224,474 A | 7/1993 | Bloomfield |
| 5,227,764 A | 7/1993 | Umemoto |
| 5,228,586 A | 7/1993 | Fuchs |
| 5,242,067 A | 9/1993 | Garby et al. |
| 5,243,970 A | 9/1993 | Ambrosio et al. |
| 5,261,548 A | 11/1993 | Barker et al. |
| 5,263,475 A | 11/1993 | Altermatt et al. |
| 5,284,133 A | 2/1994 | Burns et al. |
| 5,289,946 A | 3/1994 | Fuchs |
| 5,299,701 A | 4/1994 | Barker et al. |
| 5,300,042 A | 4/1994 | Kossoff et al. |
| 5,301,873 A | 4/1994 | Burke et al. |

(56) References Cited

U.S. PATENT DOCUMENTS

| | | |
|---|---|---|
| 5,328,597 A | 7/1994 | Boldt, Jr. et al. |
| 5,331,953 A | 7/1994 | Andersson et al. |
| 5,335,823 A | 8/1994 | Fuchs et al. |
| 5,349,944 A | 9/1994 | Chippendale et al. |
| 5,349,945 A | 9/1994 | Wass et al. |
| 5,356,012 A | 10/1994 | Tang et al. |
| 5,363,842 A | 11/1994 | Mishelevich et al. |
| 5,370,267 A | 12/1994 | Schroeder |
| 5,382,243 A | 1/1995 | Mulholland |
| RE34,847 E | 2/1995 | Muderlak et al. |
| 5,388,572 A | 2/1995 | Mulhauser et al. |
| 5,392,768 A | 2/1995 | Johansson et al. |
| 5,394,866 A | 3/1995 | Ritson et al. |
| 5,397,028 A | 3/1995 | Jesadanont |
| 5,411,173 A | 5/1995 | Weinstein |
| 5,421,482 A | 6/1995 | Garby et al. |
| 5,437,270 A | 8/1995 | Braithwaite |
| 5,447,150 A | 9/1995 | Bacon |
| 5,448,042 A | 9/1995 | Robinson et al. |
| 5,482,030 A | 1/1996 | Klein |
| 5,482,163 A | 1/1996 | Hoffman |
| 5,505,192 A | 4/1996 | Samiotes et al. |
| 5,505,195 A | 4/1996 | Wolf et al. |
| 5,509,905 A | 4/1996 | Michel |
| 5,519,197 A | 5/1996 | Robinson et al. |
| 5,520,166 A | 5/1996 | Ritson et al. |
| 5,522,378 A | 6/1996 | Ritson et al. |
| 5,544,647 A | 8/1996 | Jewett et al. |
| 5,549,101 A | 8/1996 | Trofast et al. |
| 5,564,414 A | 10/1996 | Walker et al. |
| 5,574,268 A | 11/1996 | Herman et al. |
| 5,611,444 A | 3/1997 | Garby et al. |
| 5,617,844 A | 4/1997 | King |
| 5,622,163 A | 4/1997 | Jewett et al. |
| 5,625,334 A | 4/1997 | Compton |
| 5,625,659 A | 4/1997 | Sears |
| 5,638,970 A | 6/1997 | Garby et al. |
| 5,657,748 A | 8/1997 | Braithwaite |
| 5,676,129 A | 10/1997 | Rocci, Jr. et al. |
| 5,685,294 A * | 11/1997 | Gupte ............... A61M 15/0028 128/203.15 |
| 5,687,710 A | 11/1997 | Ambrosio et al. |
| 5,692,492 A | 12/1997 | Bruna et al. |
| 5,694,882 A | 12/1997 | Marshall |
| 5,718,355 A | 2/1998 | Garby et al. |
| 5,724,957 A | 3/1998 | Rubsamen et al. |
| 5,732,836 A | 3/1998 | Barker et al. |
| 5,740,792 A | 4/1998 | Ashley et al. |
| 5,758,638 A | 6/1998 | Kreamer |
| 5,772,074 A | 6/1998 | Dial et al. |
| 5,794,612 A | 8/1998 | Wachter et al. |
| 5,799,651 A | 9/1998 | Garby et al. |
| 5,803,283 A | 9/1998 | Barker et al. |
| 5,809,997 A | 9/1998 | Wolf |
| 5,826,571 A | 10/1998 | Casper et al. |
| 5,829,434 A | 11/1998 | Ambrosio et al. |
| 5,845,777 A | 12/1998 | Najmi |
| 5,852,590 A | 12/1998 | De La Huerga |
| 5,871,007 A | 2/1999 | Clark, Jr. |
| 5,873,995 A | 2/1999 | Huang et al. |
| 5,882,507 A | 3/1999 | Tanner et al. |
| 5,896,990 A | 4/1999 | Barzana |
| 5,899,201 A | 5/1999 | Schultz et al. |
| 5,904,139 A | 5/1999 | Hauser |
| 5,957,896 A | 9/1999 | Bendek et al. |
| 5,988,496 A | 11/1999 | Bruna |
| 6,000,159 A | 12/1999 | Hornung |
| 6,012,450 A | 1/2000 | Rubsamen |
| 6,029,659 A | 2/2000 | O'Connor |
| 6,059,133 A | 5/2000 | Lai |
| 6,062,214 A | 5/2000 | Howlett |
| 6,076,521 A | 6/2000 | Lindahl et al. |
| 6,082,358 A | 7/2000 | Scarrott et al. |
| 6,089,180 A | 7/2000 | Nichols, Jr. |
| 6,119,684 A | 9/2000 | Nohl et al. |
| 6,138,669 A | 10/2000 | Rocci, Jr. et al. |
| 6,142,339 A | 11/2000 | Blacker et al. |
| 6,148,815 A | 11/2000 | Wolf |
| 6,149,054 A | 11/2000 | Cirrillo |
| 6,155,251 A | 12/2000 | Hauser |
| 6,161,724 A | 12/2000 | Blacker et al. |
| 6,164,494 A | 12/2000 | Marelli |
| 6,186,364 B1 | 2/2001 | Dobbs |
| 6,202,642 B1 | 3/2001 | McKinnon et al. |
| 6,223,744 B1 | 5/2001 | Garon |
| 6,234,168 B1 | 5/2001 | Bruna |
| 6,283,365 B1 | 9/2001 | Bason |
| 6,328,037 B1 | 12/2001 | Scarrott et al. |
| 6,336,453 B1 | 1/2002 | Scarrott et al. |
| 6,360,739 B1 | 3/2002 | Rand et al. |
| 6,405,727 B1 | 6/2002 | MacMichael et al. |
| 6,415,785 B1 | 7/2002 | Stage |
| 6,425,392 B1 | 7/2002 | Sosiak |
| 6,431,168 B1 | 8/2002 | Rand et al. |
| 6,435,372 B1 | 8/2002 | Blacker |
| 6,446,627 B1 | 9/2002 | Bowman et al. |
| 6,474,331 B1 | 11/2002 | Rand et al. |
| 6,481,438 B1 | 11/2002 | Gallem et al. |
| 6,484,717 B1 | 11/2002 | Dagsland et al. |
| 6,516,799 B1 | 2/2003 | Greenwood et al. |
| 6,529,446 B1 | 3/2003 | De La Huerga |
| 6,561,384 B2 | 5/2003 | Blacker et al. |
| 6,601,582 B2 | 8/2003 | Rand et al. |
| 6,615,827 B2 | 9/2003 | Greenwood et al. |
| 6,659,307 B1 | 12/2003 | Stradella |
| 6,679,251 B1 | 1/2004 | Gallem et al. |
| 6,701,917 B2 | 3/2004 | O'Leary |
| 6,718,972 B2 | 4/2004 | O'Leary |
| 6,729,330 B2 | 5/2004 | Scarrott et al. |
| 6,752,153 B1 | 6/2004 | Eckert |
| 6,761,161 B2 | 7/2004 | Scarrott et al. |
| 6,766,799 B2 | 7/2004 | Edwards et al. |
| 6,769,601 B2 | 8/2004 | Haikarainen et al. |
| 6,805,116 B2 | 10/2004 | Hodson |
| 6,907,876 B1 | 6/2005 | Clark et al. |
| 6,926,002 B2 | 8/2005 | Scarrott et al. |
| 6,953,039 B2 | 10/2005 | Scarrott et al. |
| 7,004,164 B2 | 2/2006 | Scarrott |
| 7,100,530 B2 | 9/2006 | Lu |
| 7,107,986 B2 | 9/2006 | Rand et al. |
| 7,137,391 B2 | 11/2006 | Bruna |
| 7,143,764 B1 | 12/2006 | Dagsland et al. |
| 7,156,258 B2 | 1/2007 | Eckert |
| 7,191,918 B2 | 3/2007 | Ouyang et al. |
| 7,195,134 B2 | 3/2007 | Ouyang et al. |
| 2002/0000225 A1 | 1/2002 | Schuler et al. |
| 2002/0153005 A1 | 10/2002 | Scarrott et al. |
| 2003/0183225 A1 | 10/2003 | Knudsen |
| 2003/0200964 A1 | 10/2003 | Blakley et al. |
| 2003/0205227 A1 | 11/2003 | Hodson |
| 2003/0209239 A1 | 11/2003 | Rand et al. |
| 2004/0065326 A1* | 4/2004 | MacMichael ....... A61M 15/009 128/205.23 |
| 2004/0069301 A1 | 4/2004 | Bacon |
| 2004/0094147 A1 | 5/2004 | Schyra et al. |
| 2004/0144798 A1 | 7/2004 | Ouyang et al. |
| 2004/0149772 A1 | 8/2004 | Ouyang |
| 2004/0149773 A1 | 8/2004 | Ouyang et al. |
| 2004/0221840 A1 | 11/2004 | Stockman-Lamb |
| 2004/0255935 A1 | 12/2004 | Bruna |
| 2004/0255936 A1 | 12/2004 | Urbanus |
| 2005/0011515 A1 | 1/2005 | Lee et al. |
| 2005/0056276 A1 | 3/2005 | Schuler et al. |
| 2005/0205512 A1 | 9/2005 | Scarrott et al. |
| 2005/0268905 A1 | 12/2005 | Rasmussen et al. |
| 2005/0284471 A1 | 12/2005 | Bruna |
| 2006/0096594 A1* | 5/2006 | Bonney ............... G06M 1/028 128/202.17 |
| 2006/0150976 A1 | 7/2006 | Scarrott et al. |
| 2006/0162724 A1 | 7/2006 | Scarrott et al. |
| 2006/0175345 A1 | 8/2006 | Lu et al. |
| 2006/0180606 A1 | 8/2006 | Lu et al. |
| 2006/0254581 A1 | 11/2006 | Genova et al. |

(56) References Cited

U.S. PATENT DOCUMENTS

| | | | |
|---|---|---|---|
| 2007/0084462 A1 | 4/2007 | Allen et al. | |
| 2007/0119450 A1* | 5/2007 | Wharton | A61M 15/0023 128/200.23 |
| 2008/0105253 A1 | 5/2008 | Pearson et al. | |

FOREIGN PATENT DOCUMENTS

| | | |
|---|---|---|
| CA | 2 152 088 A | 7/1994 |
| CA | 2 181 789 C | 6/1996 |
| CA | 2 486 892 A1 | 12/1998 |
| CA | 2 315 777 A1 | 7/1999 |
| CA | 2604067 A1 | 7/1999 |
| CA | 2 331 179 A1 | 11/1999 |
| CA | 2 383 425 A1 | 3/2001 |
| CA | 2 388 958 A1 | 3/2001 |
| CA | 2414 118 A1 | 1/2002 |
| CA | 2 420 171 A1 | 3/2002 |
| CA | 2592413 A1 | 7/2006 |
| DE | 6 603 758 | 7/1969 |
| DE | 27 02 539 A1 | 1/1977 |
| DE | 3336486 A1 | 4/1984 |
| DE | 8 590 143.1 | 10/1985 |
| DE | 86 02 238.5 | 5/1986 |
| EP | 0 028 929 A2 | 5/1981 |
| EP | 0 098 939 A2 | 1/1984 |
| EP | 114617 A2 | 8/1984 |
| EP | 0 063 599 | 6/1986 |
| EP | 0 230 323 B1 | 7/1987 |
| EP | 0 236 871 A2 | 9/1987 |
| EP | 0 288 929 A2 | 5/1988 |
| EP | 0 269 496 A2 | 6/1988 |
| EP | 280 104 B1 | 8/1988 |
| EP | 0 488 609 A1 | 6/1992 |
| EP | 0 559 757 B1 | 9/1993 |
| EP | 0 949 584 A2 | 10/1999 |
| EP | 1 369 139 A1 | 12/2003 |
| EP | 1 220 802 B1 | 2/2004 |
| FR | 2 743 055 A1 | 7/1997 |
| GB | 998148 | 7/1965 |
| GB | 1058636 | 2/1967 |
| GB | 1 290 484 | 9/1972 |
| GB | 1317315 | 5/1973 |
| GB | 2 036 695 A | 7/1980 |
| GB | 2 063 075 A | 6/1981 |
| GB | 2 092 991 A | 8/1982 |
| GB | 2 104 393 A | 3/1983 |
| GB | 2 191 032 A | 12/1987 |
| GB | 2 195 544 A | 4/1988 |
| GB | 2 348 928 A | 10/2000 |
| GB | 2414 187 A | 11/2005 |
| JP | 61-55759 | 4/1986 |
| JP | 04-50059 | 4/1992 |
| JP | 6-26891 | 4/1994 |
| WO | WO 86/02275 | 4/1986 |
| WO | WO 87/04354 | 8/1987 |
| WO | WO 90/10470 | 9/1990 |
| WO | WO 91/06334 | 5/1991 |
| WO | WO 92/07600 | 5/1992 |
| WO | WO 92/09324 | 6/1992 |
| WO | WO 92/15353 | 9/1992 |
| WO | WO 92/17231 | 10/1992 |
| WO | WO 93/24167 | 12/1993 |
| WO | WO 94/11272 | 5/1994 |
| WO | WO 94/14492 | 7/1994 |
| WO | WO 95/34874 | 12/1995 |
| WO | WO 96/16686 | 6/1996 |
| WO | WO 96/16687 | 6/1996 |
| WO | WO 96/39337 | 12/1996 |
| WO | WO 98/01822 | 1/1998 |
| WO | WO 98/56444 | 12/1998 |
| WO | WO 98/56445 | 12/1998 |
| WO | WO 99/36115 | 7/1999 |
| WO | WO 99/57019 | 11/1999 |
| WO | WO 00/09187 | 2/2000 |
| WO | WO 00/59806 | 10/2000 |
| WO | WO 01/28887 A1 | 4/2001 |
| WO | WO 01/29765 | 4/2001 |
| WO | WO 01/37909 A1 | 5/2001 |
| WO | WO 03/101514 A1 | 12/2003 |
| WO | WO 03/103759 A1 | 12/2003 |
| WO | WO 04/089451 A1 | 10/2004 |
| WO | WO 2006/110080 A1 | 10/2006 |

OTHER PUBLICATIONS

Written Opinion in International Application No. PCT/IB2007/002205, dated Jan. 11, 2008, 7 pages.
International Search Report in International Application No. PCT/IB2007/002205, dated Jan. 11, 2008, 6 pages.
U.S. Department of Health and Human Services, Food and Drug Administration, Center for Drug Evaluation and Research (ODER)—Clinical, "Guidance for Industry: Integration of Dose-Counting Mechanisms into MDI Drug Products—Draft Guidance," dated Nov. 2001,6 pages.
English language translation of Office Action in Japanese Application No. 2008-019458 dispatched Sep. 29, 2009, 2 pages.

* cited by examiner

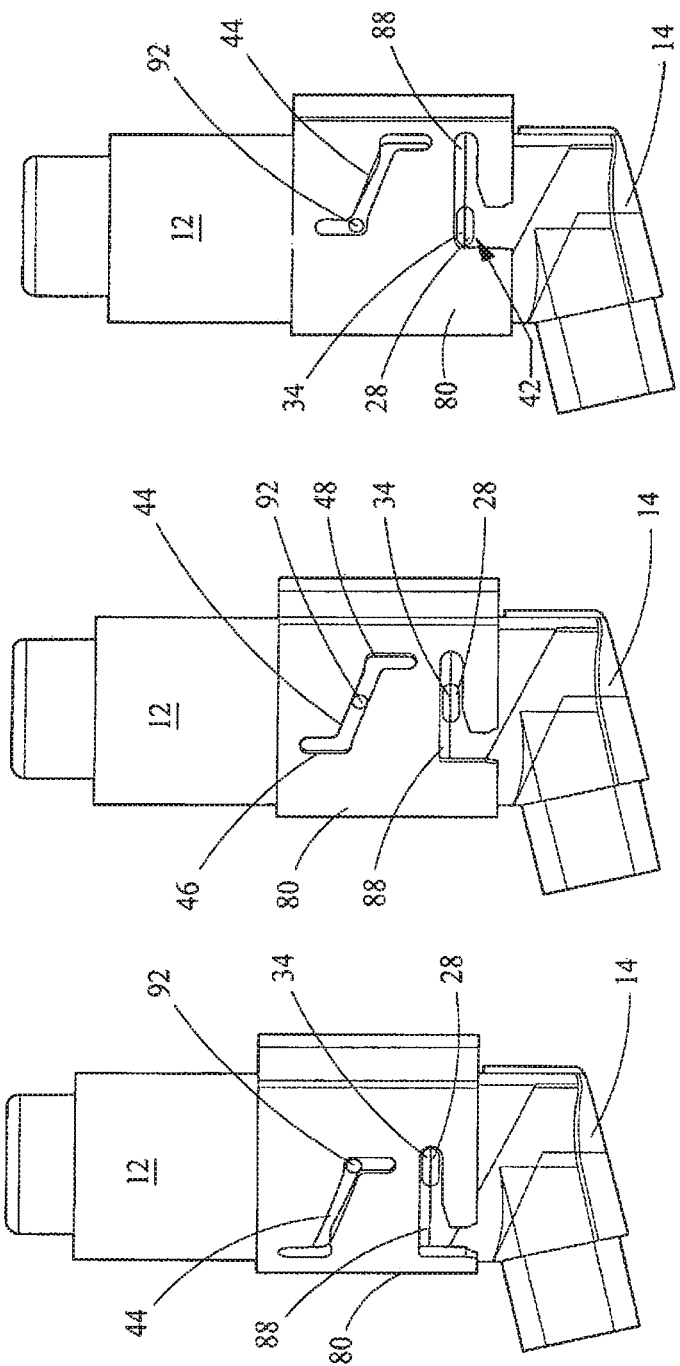

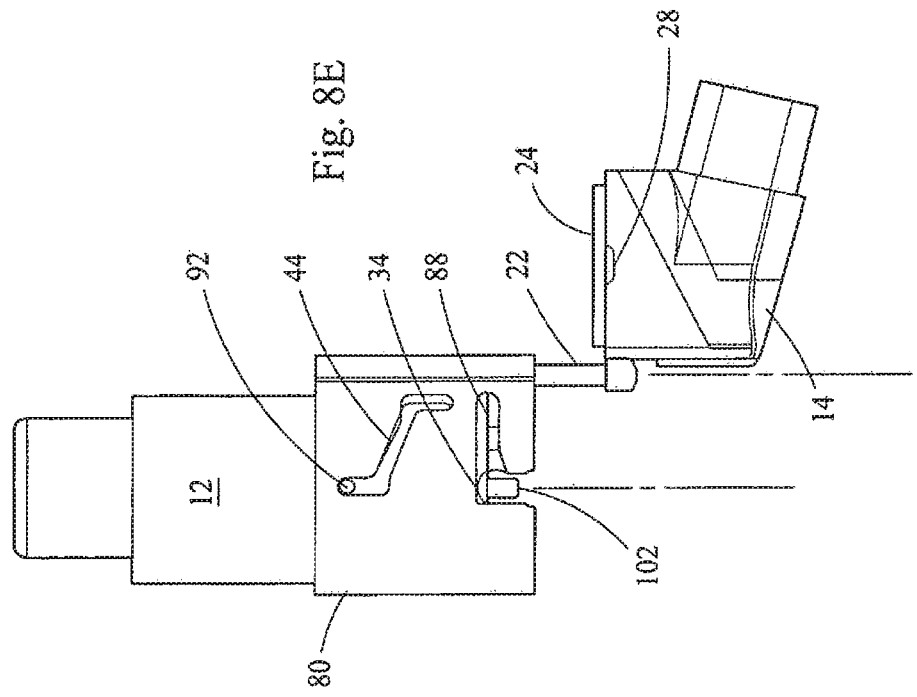
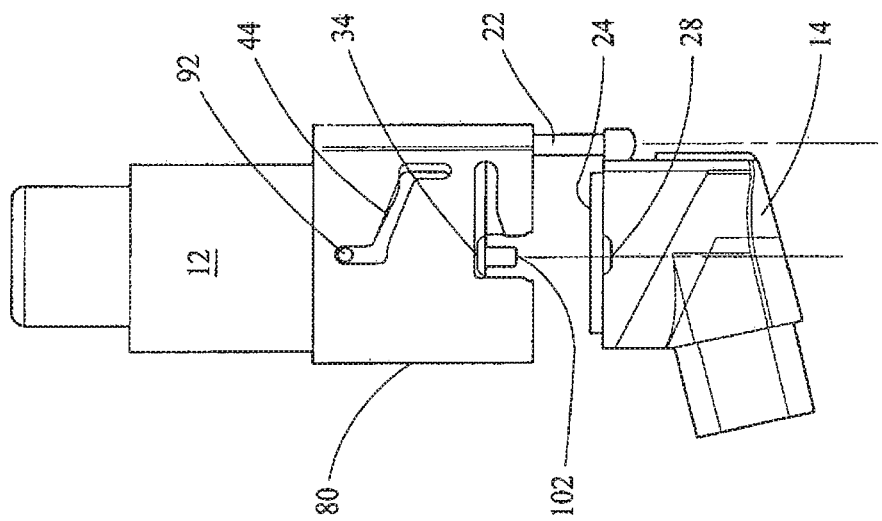

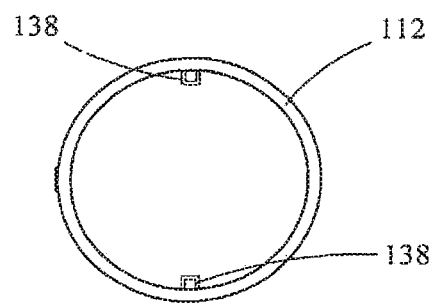
Fig. 49
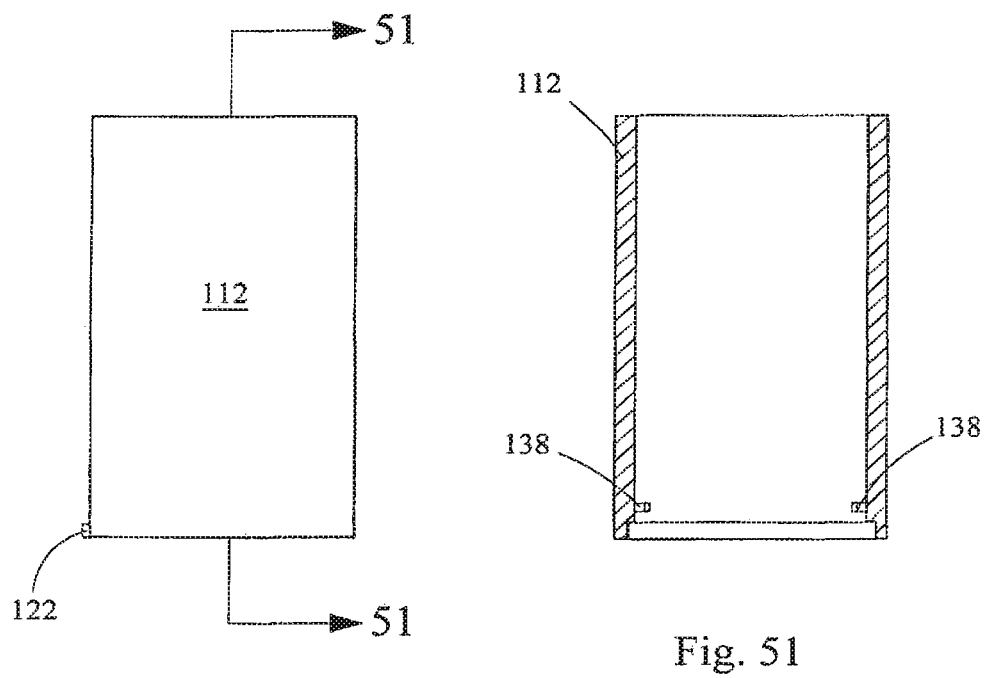
Fig. 50
Fig. 51

DISPENSING DEVICE

This application is a continuation of U.S. application Ser. No. 13/414,411, filed Mar. 7, 2012, which is a continuation of U.S. application Ser. No. 11/888,308, filed Jul. 31, 2007, which application claims the benefit of U.S. Provisional Application No. 60/834,764, filed Aug. 1, 2006, the entire disclosures of which are hereby incorporated herein by reference.

FIELD OF THE INVENTION

The present invention relates generally to a dispensing device, and in particular, to a dispensing device having a dosage indicator for indicating the number of metered dosages that have been dispensed from, or remain in, a container that is associated with that particular dispensing device.

BACKGROUND

Aerosol dispensing devices have been developed that include a dose indicating device to indicate the number of metered doses that have been dispensed from the device, or to indicate the number of doses remaining therein. For example, patients have certain conditions that can be treated with medicaments dispensed in an aerosol and administered to the patient by inhalation. In one format, the aerosol with medicaments are contained in a container, and dispensed in metered, or measured, dosages with an inhalation device, or actuator boot. In such an arrangement, it can be important for the patient to be able to ascertain the number of metered doses remaining in the container, either by an indication of the number remaining therein or by knowledge of the number already dispensed therefrom, such that the patient is not caught unaware with an empty container when in need of the medicament. Thus, it may be important for the inhalation device to provide an accurate indication of either the number of doses remaining in the container, or the number of doses already dispensed therefrom.

In some embodiments, for example metered dose inhalers configured with containers holding HFA propellant, the actuator nozzle or well may need to be cleaned periodically to ensure proper aerosol drug delivery and output. In conventional embodiments, the container is simply removed from the actuator and water is used to clear the actuator nozzle. However, when the dispensing device is configured with an indicator device, for example a device located in the actuator boot, there is potential for a different container to be associated with the actuator boot and indicator device, thereby leading to an inaccurate count of dosages dispensed from or remaining in that container.

SUMMARY

Briefly stated, in one aspect the invention is directed to a dispenser that dispenses dosages of a substance. The dispenser includes a container having an end portion and a valve stem extending from the end portion. A dispenser housing includes a nozzle having a well. An indicating device is connected to the dispenser housing and includes an indicator with dosage indicia. The container is moveable between an engaged position, wherein the valve stem is disposed in the well and a disengaged position, wherein the valve stem is removed from the well. In the disengaged position, the actuator nozzle is accessible for cleaning without getting water on the valve stem. A connection is maintained between the container and the dispenser housing, however, such that the same container is associated with the dispenser housing and indicating device thereby maintaining the count integrity of the device.

In one embodiment, the dispenser housing includes an upper portion pivotally connected to a lower portion. The indicating device is connected to the lower portion, while the container is moveably connected to the upper portion. The upper and lower portions are pivotable between at least a first and second position.

In one embodiment, the upper portion is pivotal relative to the lower portion about a longitudinal axis. In another embodiment, the upper portion is pivotal relative to the lower portion about an axis non-parallel to the longitudinal axis, and preferably about an axis substantially perpendicular to the longitudinal axis.

In one embodiment, a locking collar maintains a fixed connection of the upper and lower portions when the container is engaged with the support block. The locking collar is moveable so as to disengage the container from the support block and unlock or release the upper portion from the lower portion, such that the upper portion, with the container coupled thereto, can be pivoted relative to the lower portion.

In yet another aspect, a method for dispensing dosages from the container and for disengaging the container from the support block while maintaining a connection with the dispenser housing is provided.

The various embodiments provide simple, robust and inexpensive solutions for providing the user with information allowing them to ascertain the number of metered doses remaining in the container, either by an indication of the number remaining therein or by knowledge of the number already dispensed therefrom. In addition, the container remains connected to the dispenser housing, even if it is disengaged from the support block, for example to clean the housing, thereby ensuring that the integrity of the dose count for the container is preserved and also that the container will be used with a properly configured dispenser housing. In the latter situation, it should be understood that the dispenser housing and container can be used without an indicating device.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

BRIEF DESCRIPTION OF THE DRAWINGS

FIGS. 8A-8E are side views of the dispensing device shown in FIG. 1B as the device is moved from a ready-to-use configuration to a ready-to-clean configuration.

FIG. 49 is a top view of the upper portion of the dispenser housing.

FIG. 50 is a side view of the upper portion.

FIG. 51 is a cross-sectional view of the upper portion shown in FIG. 50 taken along line 51-51.

DETAILED DESCRIPTION OF THE PRESENTLY PREFERRED EMBODIMENTS

Figure 1A:
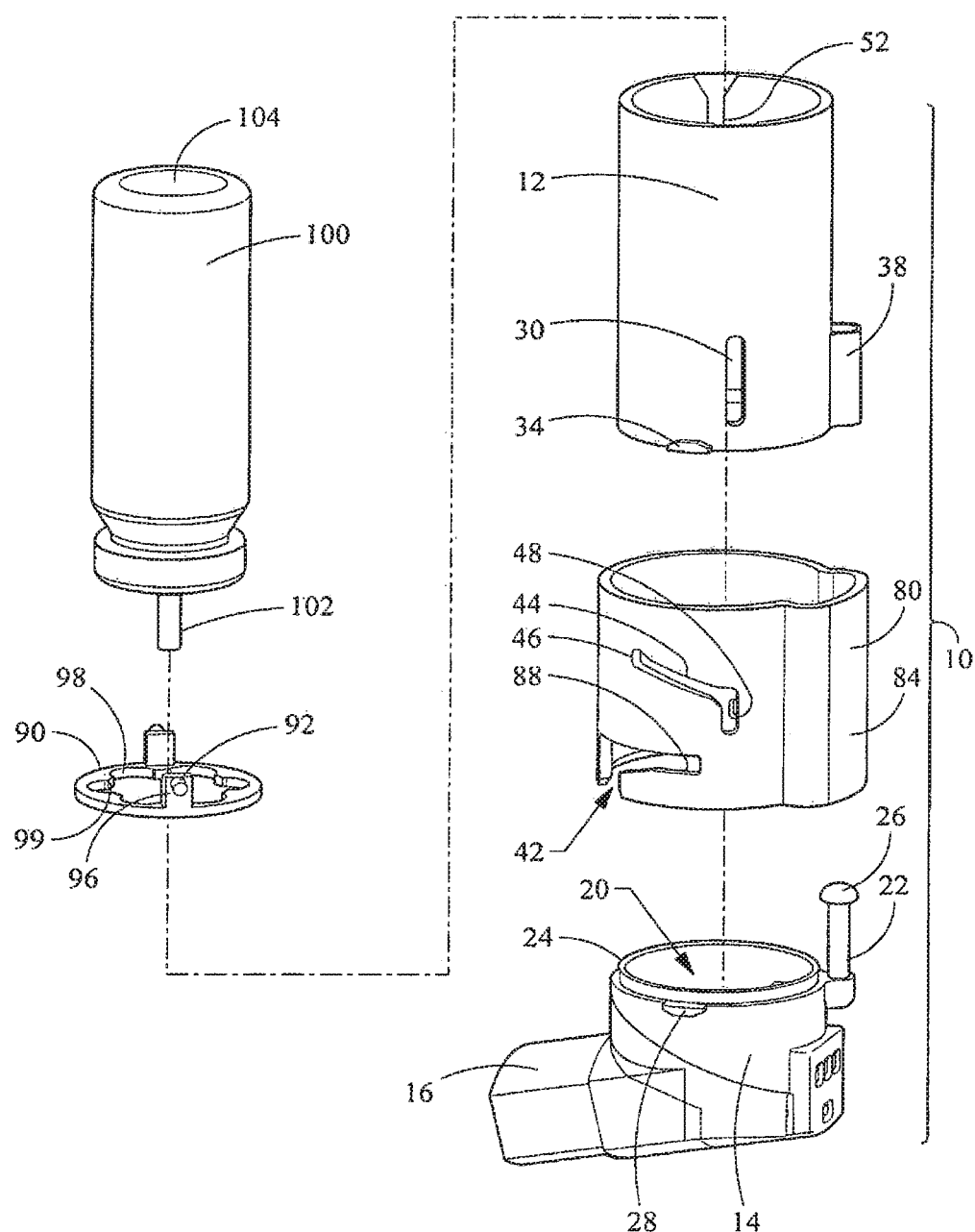
FIG. 1A is an exploded perspective view of a first embodiment of a dispensing device.
Figure 1B:
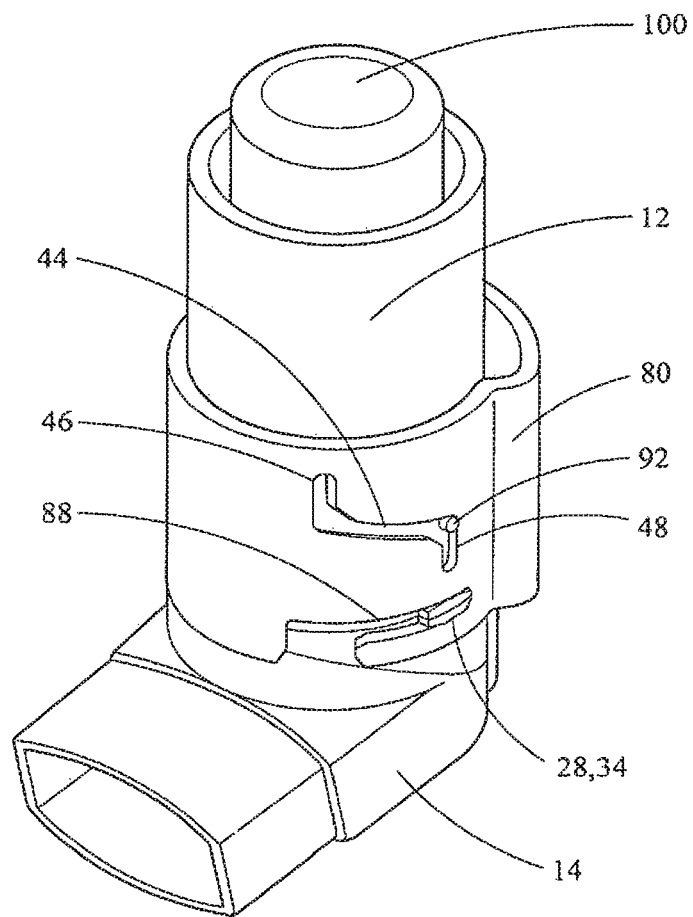
FIG. 1B is an assembled perspective view of the dispensing device shown in FIG. 1A.
Figure 2:
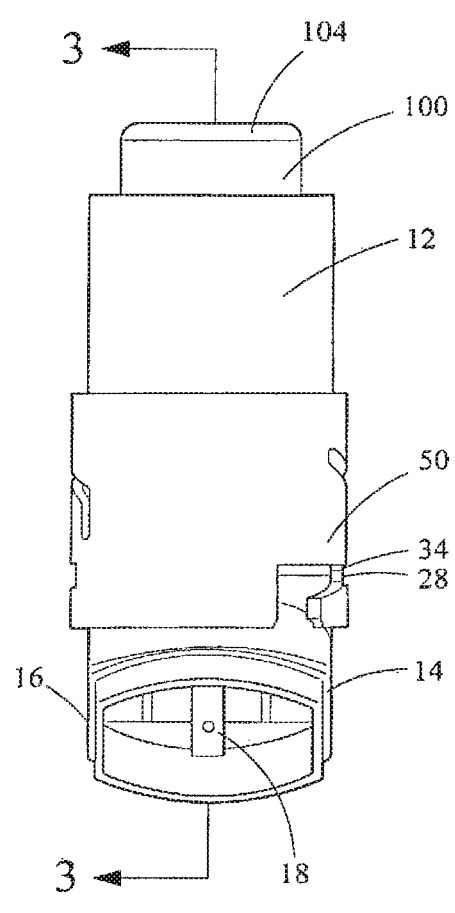
FIG. 2 is a front view of the dispensing device shown in FIG. 1B.
Figure 3:
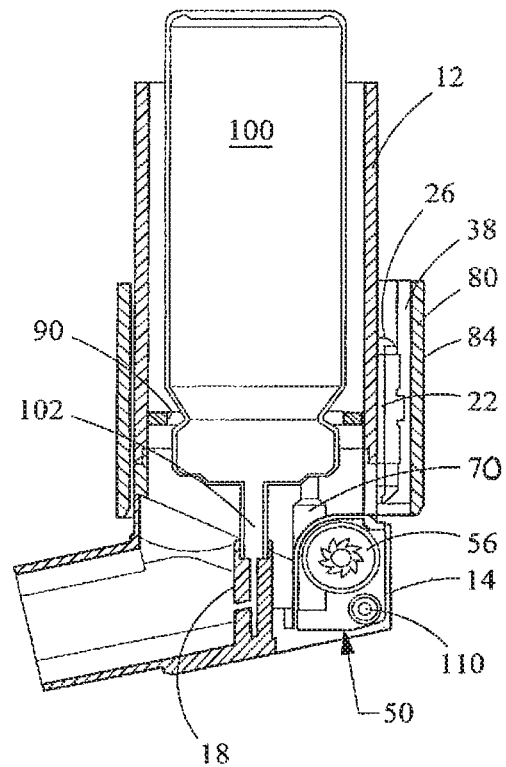
FIG. 3 is partial cross-sectional view of the dispensing device shown in FIG. 2 taken along line 3-3.
Figure 4:
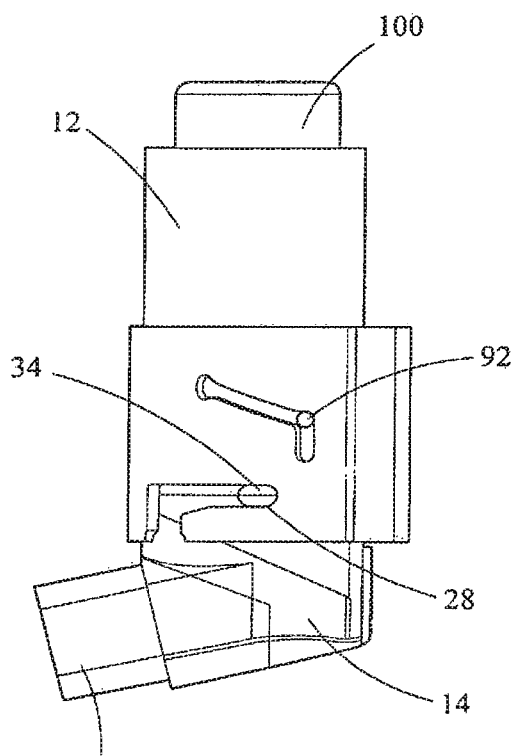
FIG. 4 is a side view of the dispensing device shown in FIG. 1B.
Figure 5:
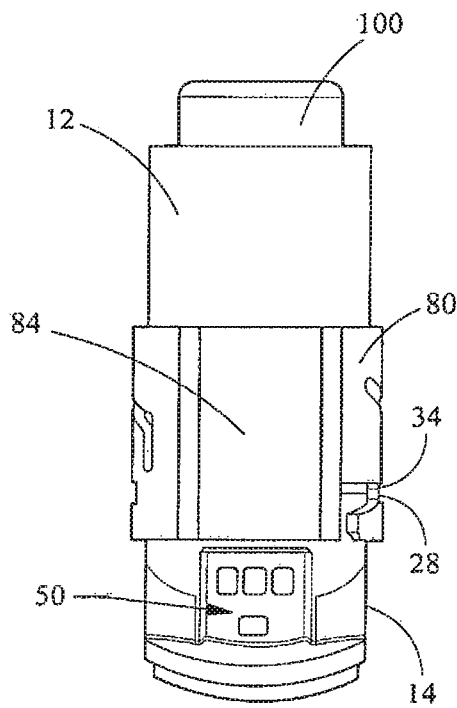
FIG. 5 is a rear view of the dispensing device shown in FIG. 1B.
Figure 6:
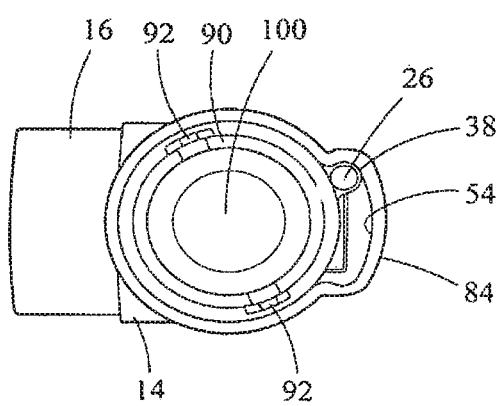
FIG. 6 is a top view of the dispensing device shown in FIG. 1B.
Figure 7:
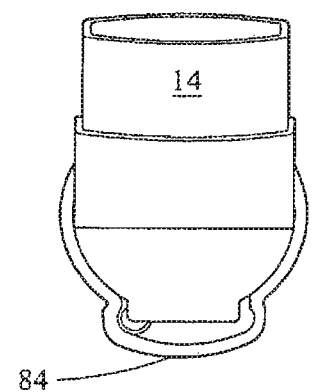
FIG. 7 is a bottom view of the dispensing device shown in FIG. 1B.
Figure 9:
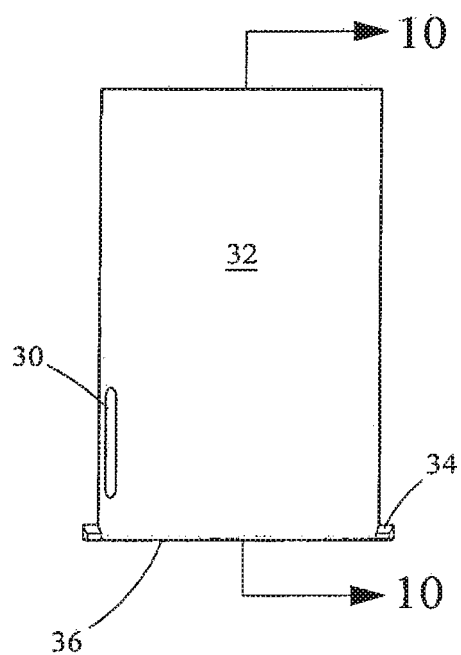
FIG. 9 is a first side view of an upper portion of the dispenser housing.
Figure 10:
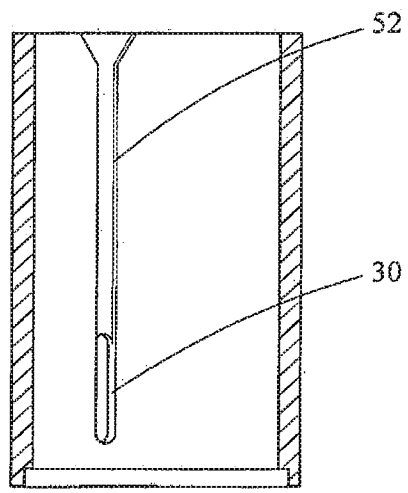
FIG. 10 is a cross-sectional view of the upper portion shown in FIG. 9 taken along line 10-10.
Figure 11:
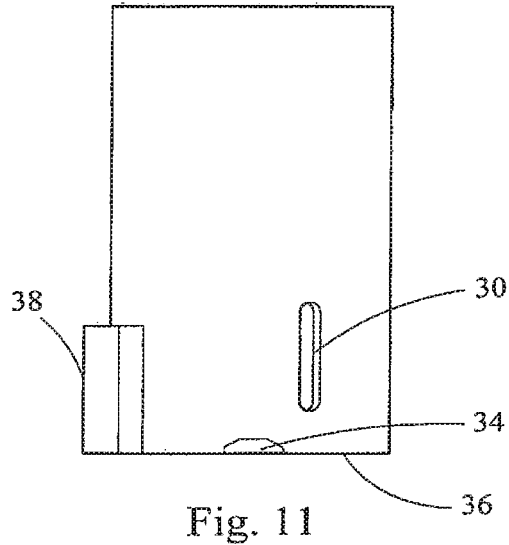
FIG. 11 is a second side view of the upper portion.
Figure 12:
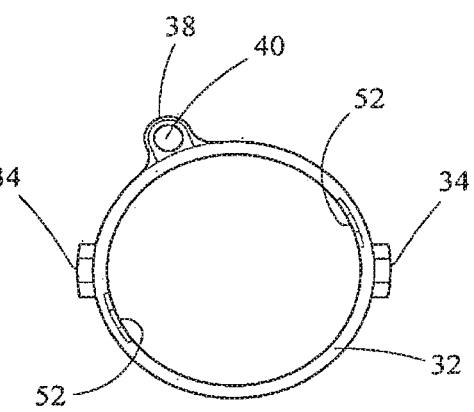
FIG. 12 is a top view of the upper portion.
Figure 13:
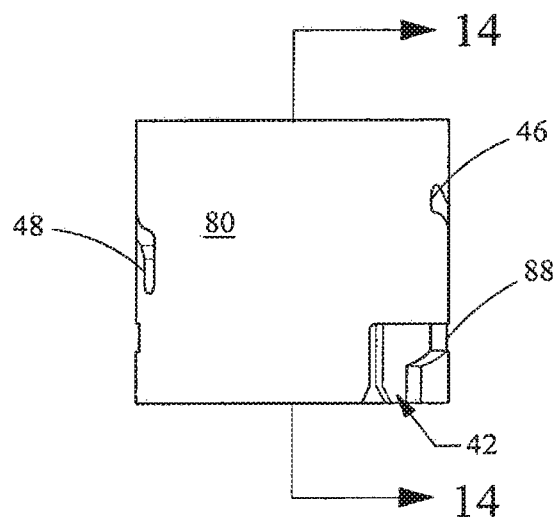
FIG. 13 is a side view of a connector member.
Figure 14:
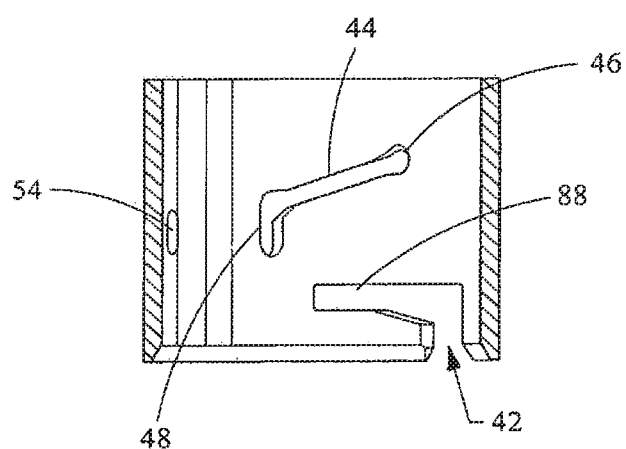
FIG. 14 is a cross-sectional view of the connector member shown in FIG. 13 taken along line 14-14.
Figure 15:
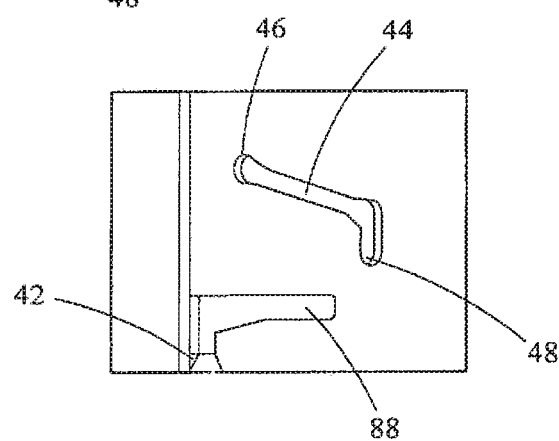
FIG. 15 is another side view of the connector member.
Figure 16:
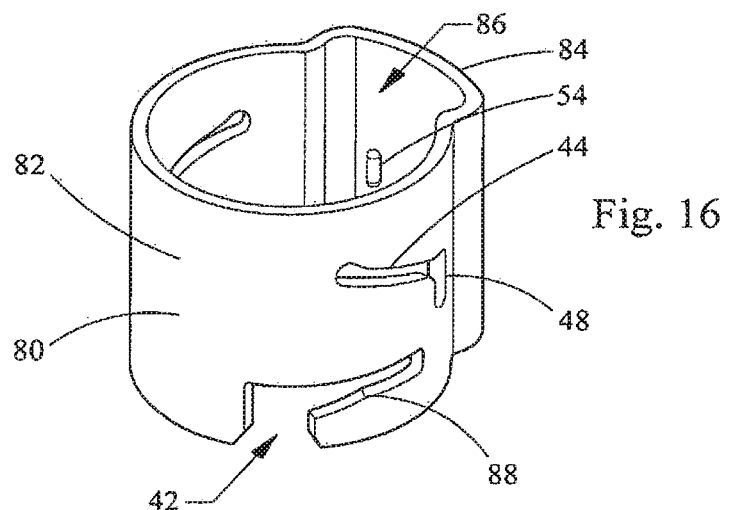
FIG. 16 is a perspective view of the connector.
Figure 17:
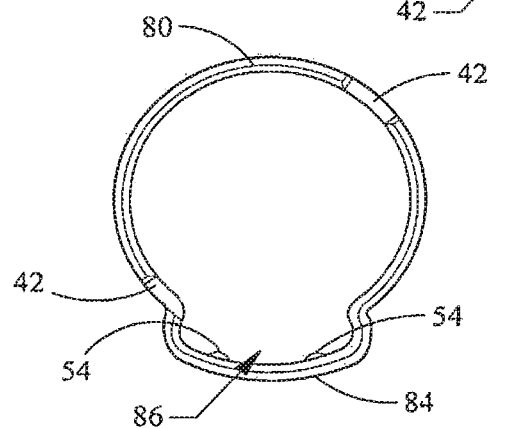
FIG. 17 is a top view of the connector.
Figure 18:
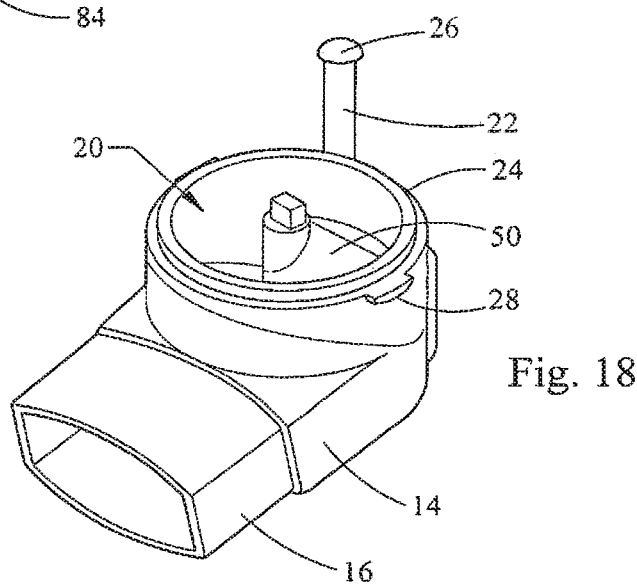
FIG. 18 is a perspective view of a lower portion of the dispenser housing.
Figure 19:
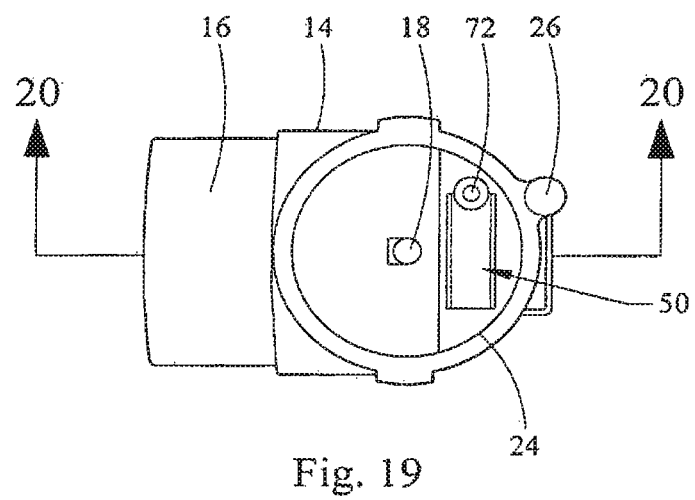
FIG. 19 is a top view of the lower portion.
Figure 20:
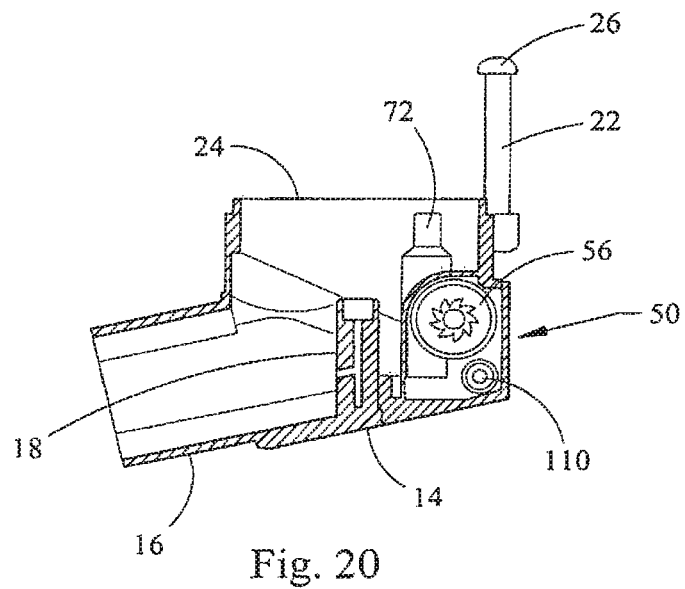
FIG. 20 is a cross-sectional view of the lower portion shown in FIG. 19 taken along line 20-20.
Figure 21:
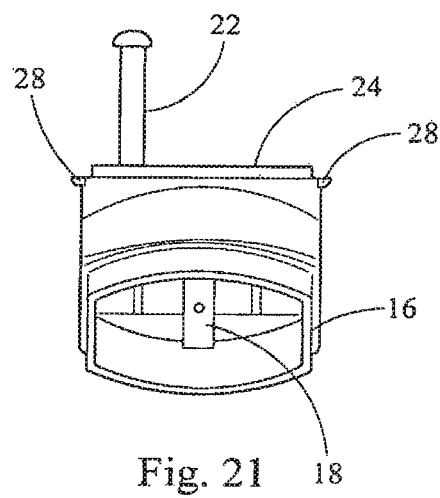
FIG. 21 is a front view of the lower portion.
Figure 22:
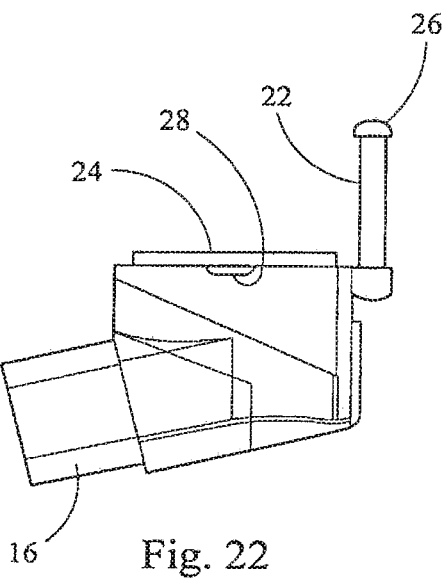
FIG. 22 is a side view of the lower portion.
Figure 23:
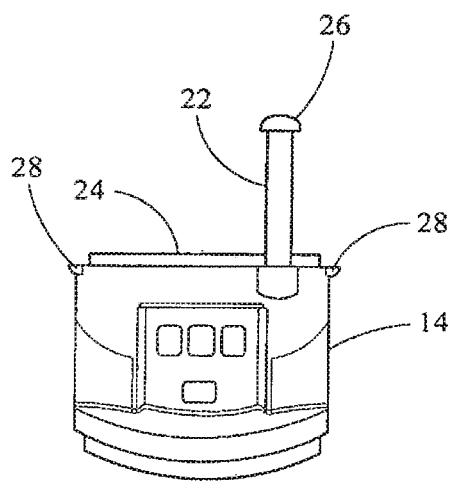
FIG. 23 is a rear view of the lower portion.
Figure 24:
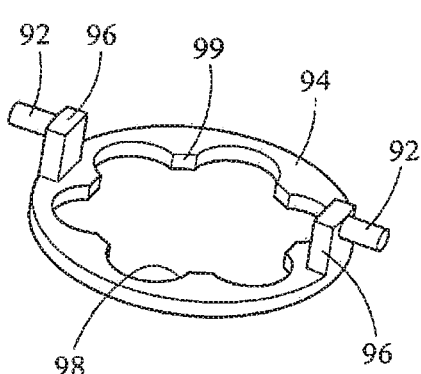
FIG. 24 is a perspective view of a retainer member.
Figure 25:
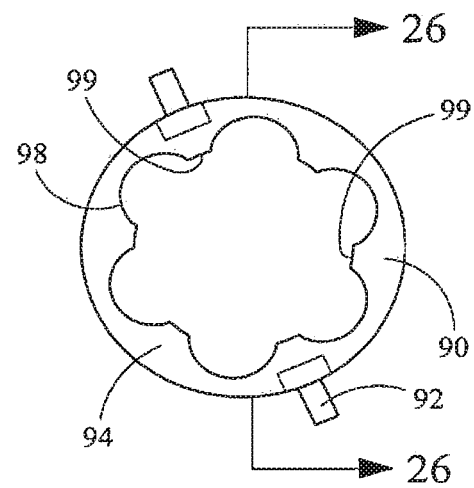
FIG. 25 is a top view of the retainer member.
Figure 26:
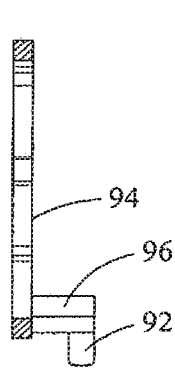
FIG. 26 is a cross-sectional view of the retainer member taken along line 26-26 of FIG. 25.
Figure 27:
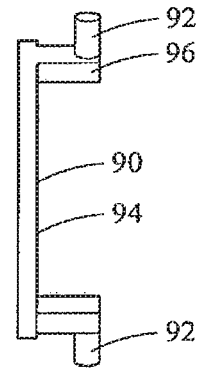
FIG. 27 is a first side view of the retainer member.
Figure 28:
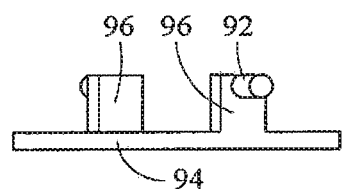
FIG. 28 is a second side view of the retainer member.
Figure 29:
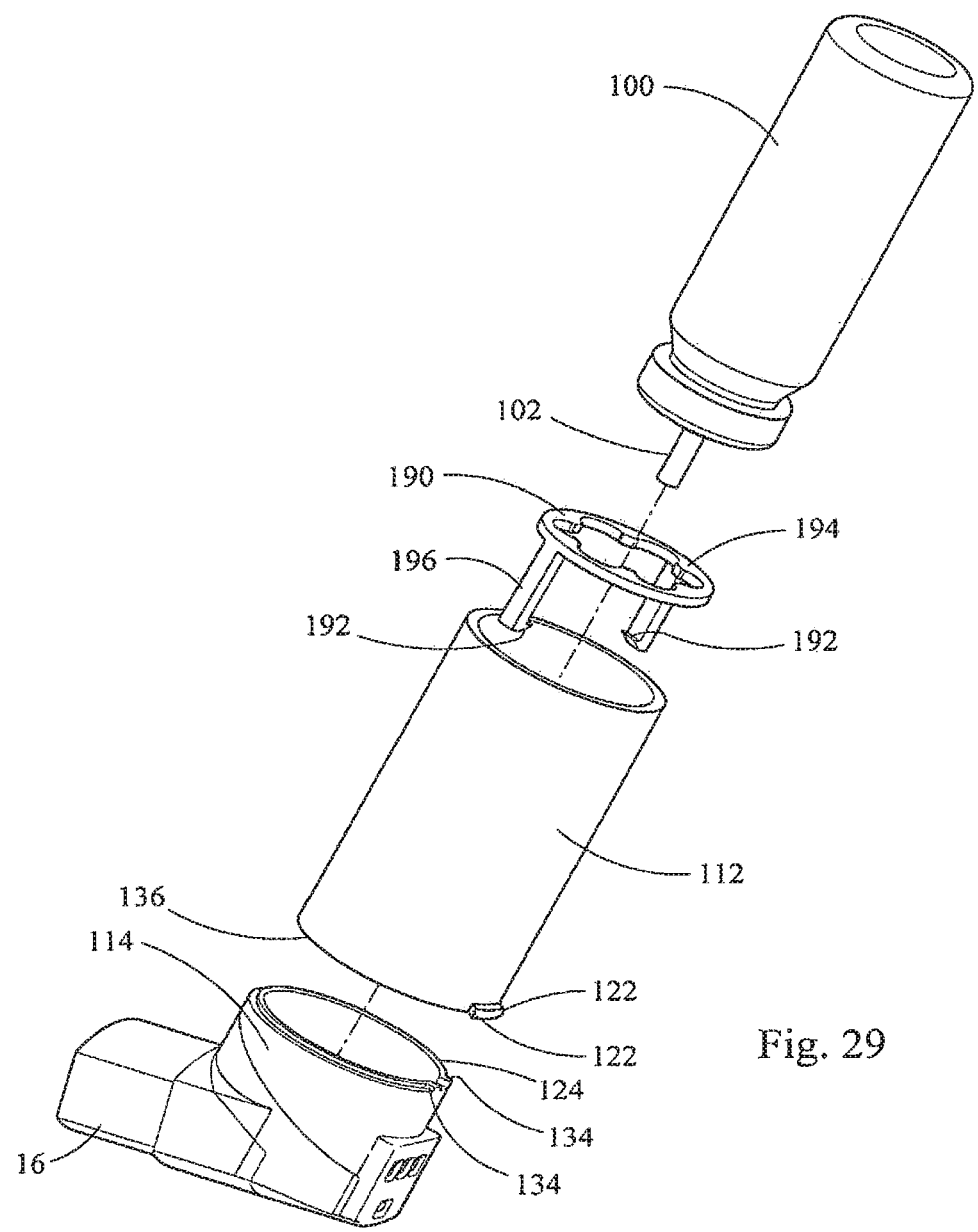
FIG. 29 is an exploded perspective view of a second embodiment of a dispensing device.
Figures 30, 31:
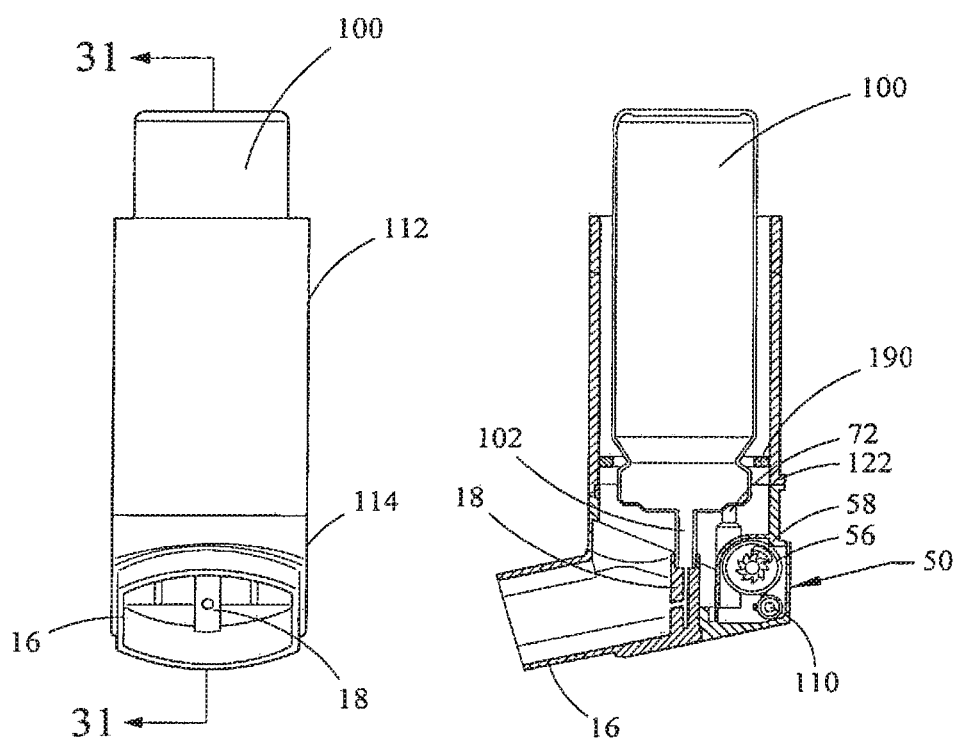
FIG. 30 is a front view of the dispensing device shown in FIG. 29.
FIG. 31 is a partial cross-sectional view of the dispensing device shown in FIG. 30 taken along line 31-31.
Figure 32:
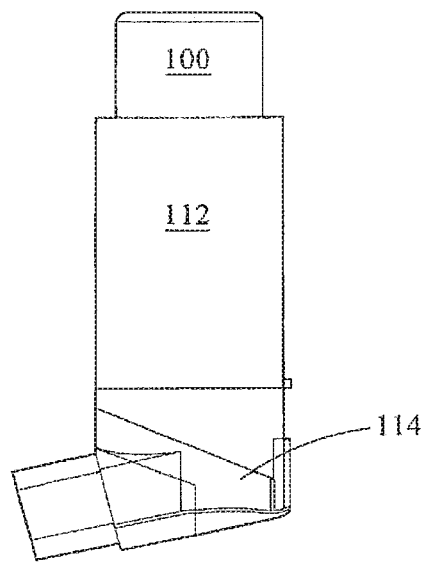
FIG. 32 is a side view of the dispensing device shown in FIG. 29.
Figure 33:
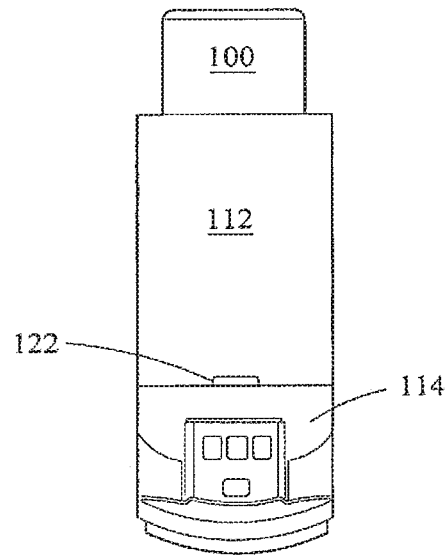
FIG. 33 is a rear view of the dispensing device shown in FIG. 29.
Figure 34:
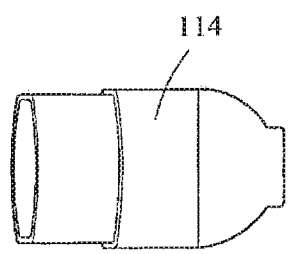
FIG. 34 is a bottom view of the dispensing device shown in FIG. 29.
Figure 35:
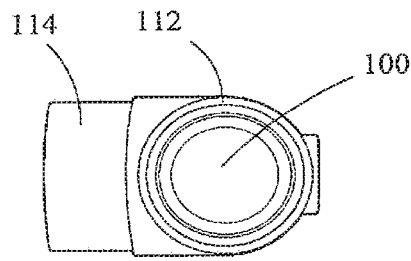
FIG. 35 is a top view of the dispensing device shown in FIG. 29.
Figure 36:
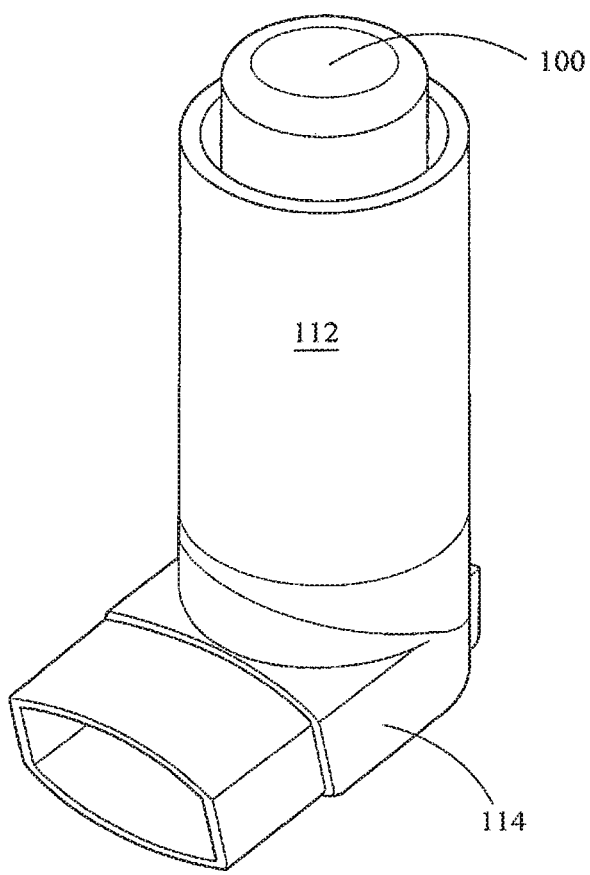
FIG. 36 is a perspective view of the assembled dispensing device shown in FIG. 29.
Figure 37:
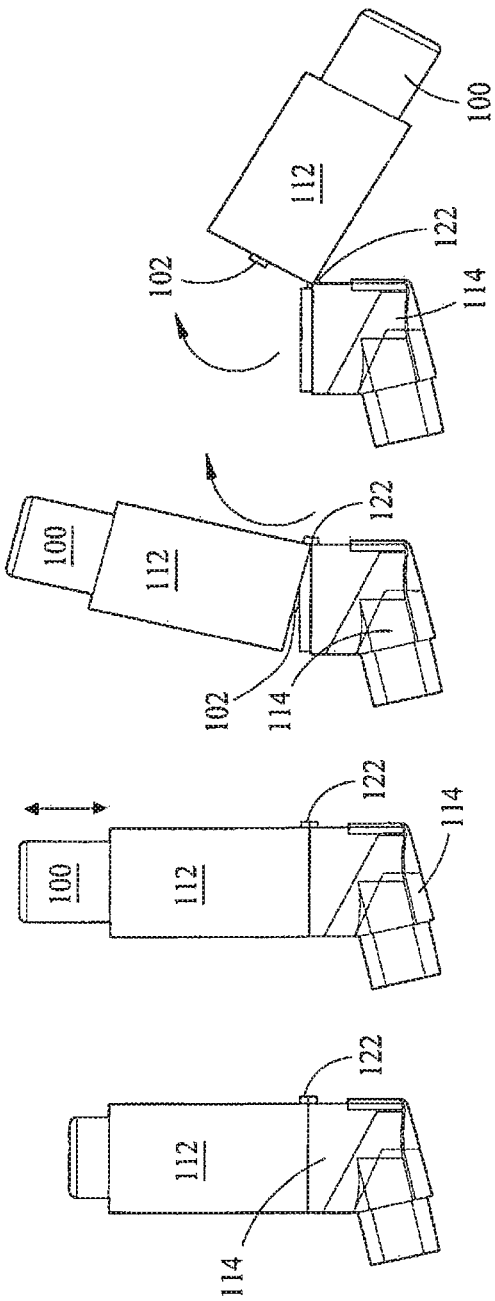
FIGS. 37A-37D are side views of the dispensing device shown in FIG. 36 as the device is moved from a ready-to-use configuration to a ready-to-clean configuration.
Figure 38:
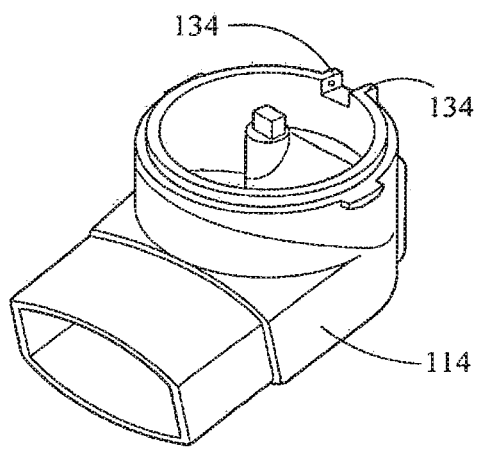
FIG. 38 is a perspective view of a lower portion of dispenser housing.
Figure 39:
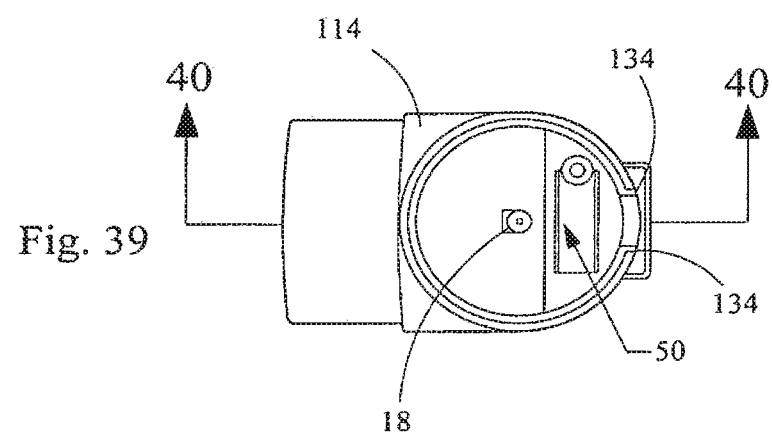
FIG. 39 is a top view of the lower portion.
Figure 40:
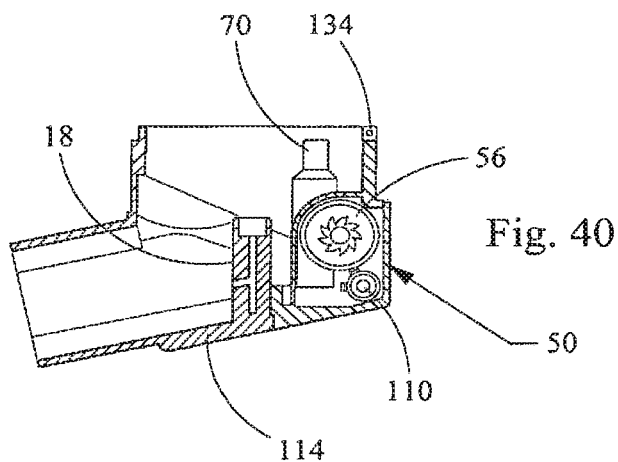
FIG. 40 is a cross-sectional view of the lower portion shown in FIG. 39 taken along line 40-40.
Figure 41:
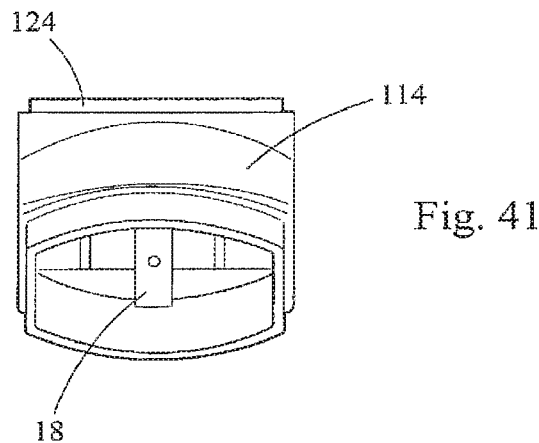
FIG. 41 is a front view of the lower portion.
Figure 42:
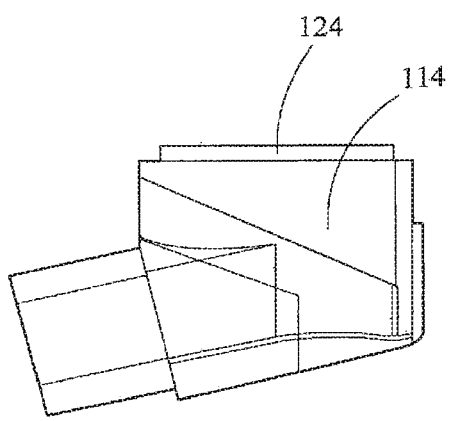
FIG. 42 is a side view of the lower portion.
Figure 43:
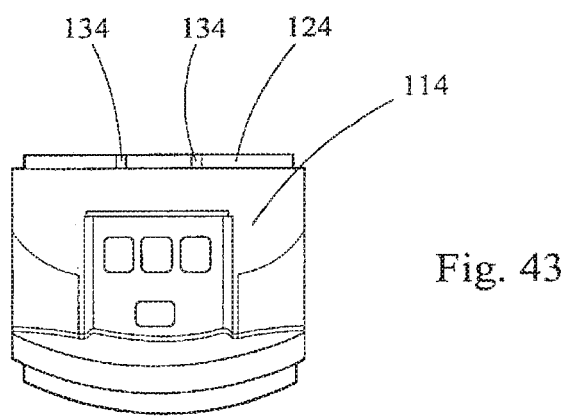
FIG. 43 is a rear view of the lower portion.
Figure 44:
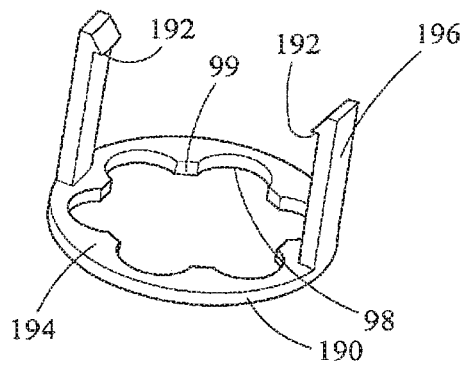
FIG. 44 is a perspective view of a retainer member.
Figure 45:
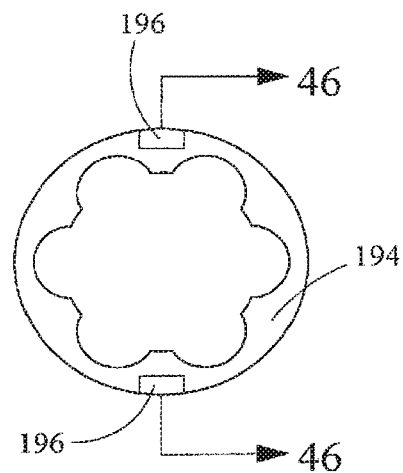
FIG. 45 a top view of the retainer member.
Figure 46:
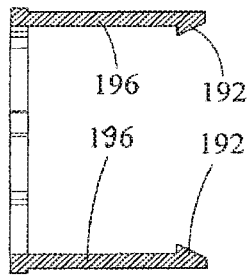
FIG. 46 is a cross-sectional view of the retainer member taken along line 46-46 of FIG. 45.
Figure 47:
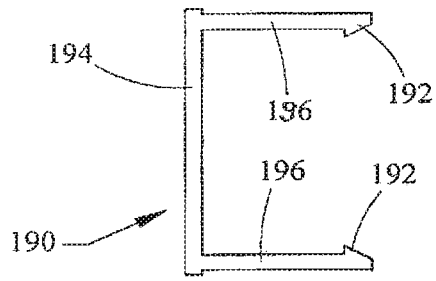
FIG. 47 is a first side view of the retainer member.
Figure 48:
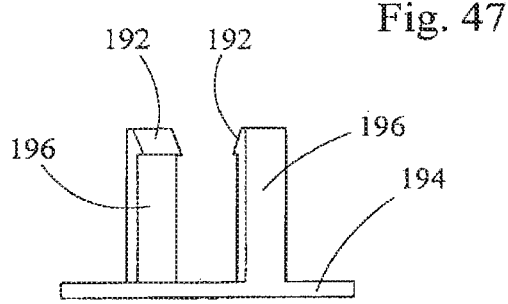
FIG. 48 is a second side view of the retainer member.
Figure 52:
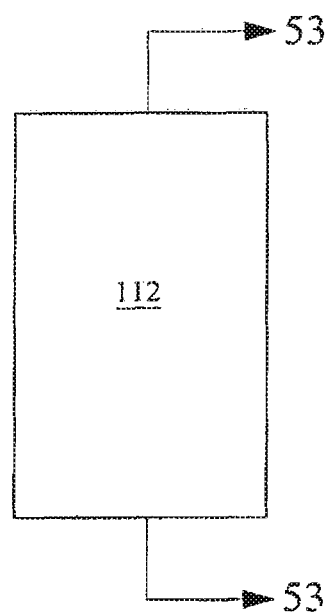
FIG. 52 is another side view of the upper portion.
Figure 53:
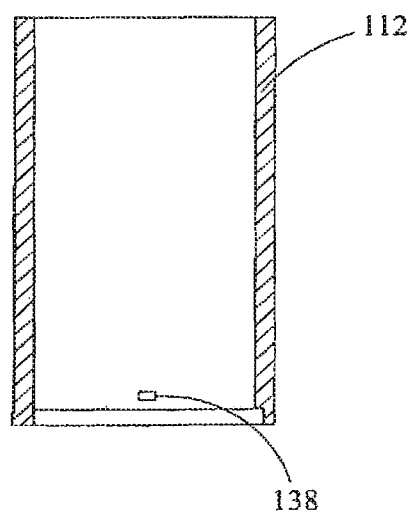
FIG. 53 is a cross-sectional view of the upper portion shown in FIG. 52 taken along line 53-53.
Figure 54A:
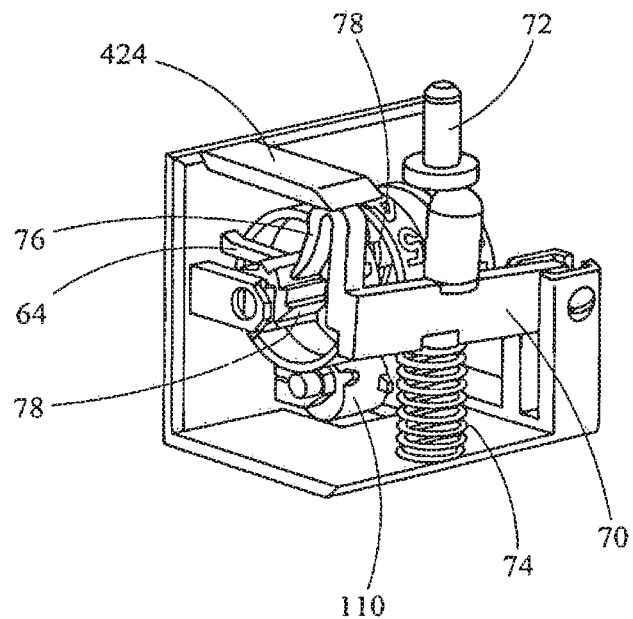
FIGS. 54A and 54B show an assembled and exploded view of a first indicator assembly.
Figure 54B:
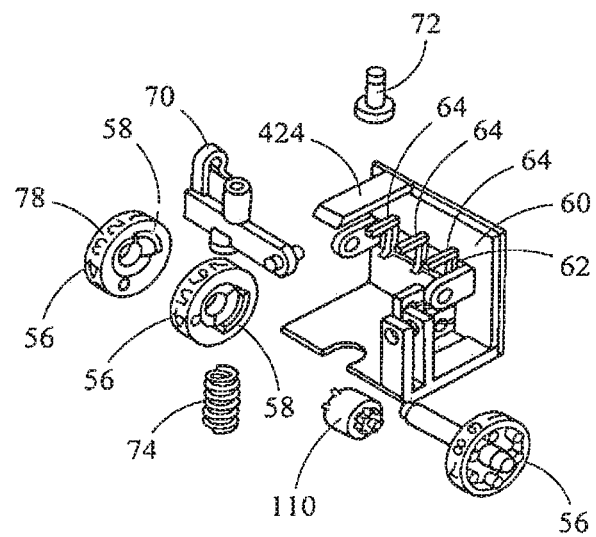
Figure 55A:
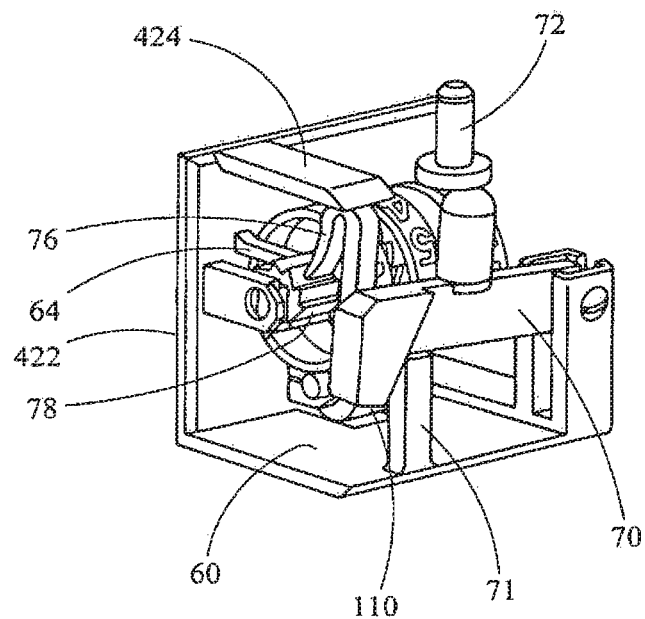
FIGS. 55A and 55B show an assembled and exploded view of a second indicator assembly.
Figure 55B:
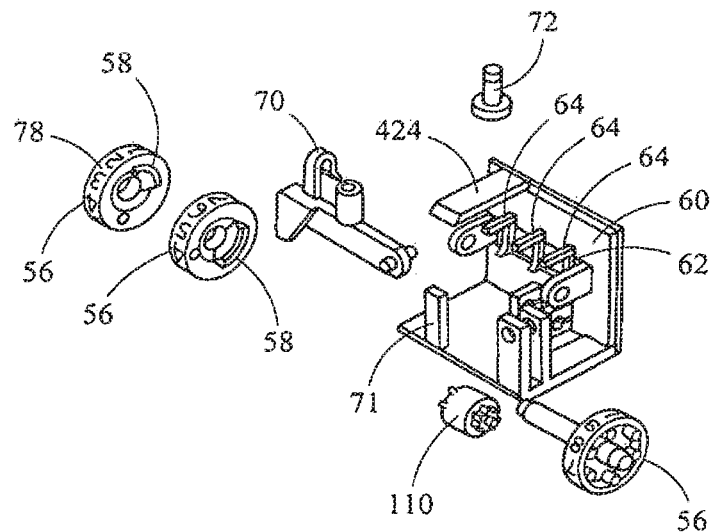
Figure 56A:
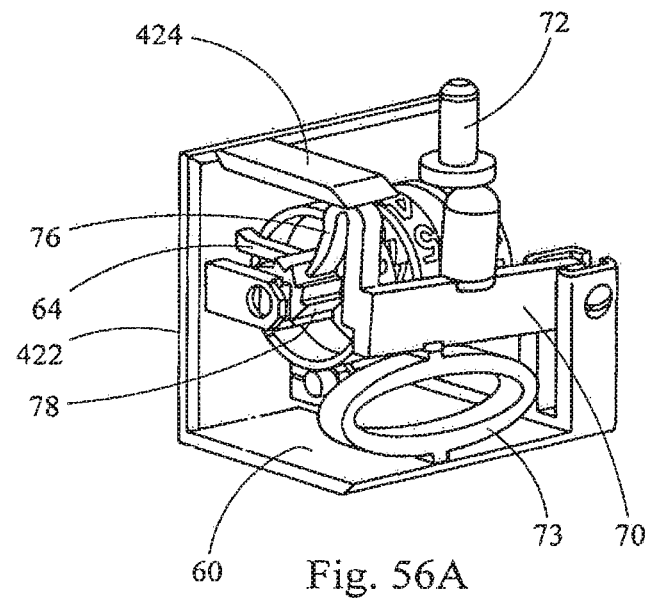
FIGS. 56A and 56B show an assembled and exploded view of a third indicator assembly.
Figure 56B:
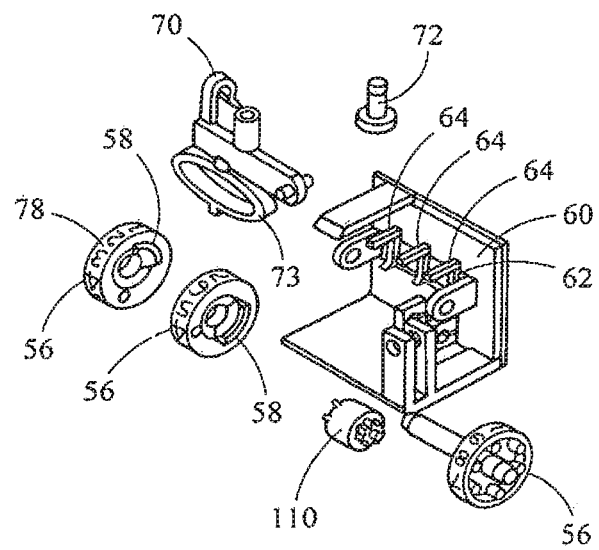

Referring to the drawings, and in particular FIGS. 1-8E and 57-62B, a dispensing device, or dispenser, is shown as including a housing 10, 310 or actuator boot, and a container 100 disposed therein. In a first embodiment, the actuator boot has an upper cylindrical portion 12, 312, referred to as a chimney, and a lower portion 14, 314.

Referring to FIGS. 1A, 18-23 and 64, the lower portion 14, 314 is configured with a mouthpiece 16, 316 and includes a support block 18 having a well for receiving the valve stem 102 of the container and a cavity 20 for receiving an indicating device 50. An orifice penetrates the support block 18, to communicate with a bottom portion of the well. The mouthpiece 16, 316 intended for insertion into the mouth of a patient, forms an exhaust port that communicates with the orifice and well. The mouthpiece 16, 316 extends laterally from the housing so as to facilitate insertion of the mouthpiece into the mouth of the patient.

A hinge post 22, 322, or pin, extends upwardly from the lower portion past an upper circumferential rim 24, 324 thereof. The hinge pin includes a head 26, 326 formed at an end thereof that functions as a stop device.

Figure 64:
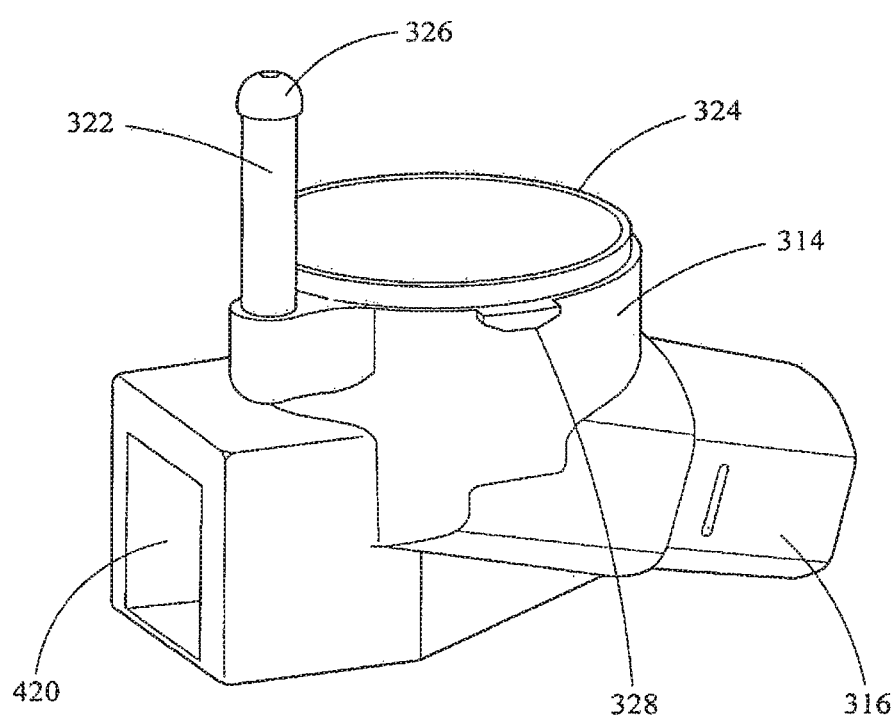
FIG. 64 is a perspective view of one embodiment of a lower portion of an actuator boot/housing.

The lower portion further includes a pair of guides or locator pins 28, 328, otherwise referred to as followers, extending radially outwardly from opposite sides of the lower portion adjacent the upper circumferential rim. It should be understood that a single lug or guide 28, 328 may suffice, or that more than two guides may be suitable for securing the lower portion to a connector member 80, 380, as shown in FIGS. 1A-8E and 59A-61B. As further discussed below, the indicating device 50 is removably or fixedly disposed in the lower portion. For example, as shown in FIGS. 61A and 64, an opening is formed in the lower portion Referring to FIGS. 1A, 9-12, 57 and 60-61B, the upper portion 12, 312 is open at both ends and includes a pair of longitudinally extending slots 30, 330 formed through a side wall 32, 332 thereof that are shaped and configured to engage a pair of lugs 92, 292, 392 or followers, formed on a retainer member 90, 290, 390 shown in FIGS. 24-28, 57 and 60. The upper portion 12, 312 further includes a pair of lugs, or guides/followers 34, 334, extending radially outwardly from the lower portion adjacent a lower circumferential rim 36, 336 thereof. The lugs 34, 334 are shaped to mate with the lugs 28 formed on the lower portion, with the lugs preferably being mirror images of each other, such that the lugs 28, 328, 34, 334 in combination form a guide. Accordingly, the number of lugs 34, 334 on the upper portion preferably matches the number of lugs 28, 328 on the lower portion, and further are spaced and configured to mate with the lugs 28, 328 on the lower portion. Of course, it should be understood that other configurations are suitable.

The upper portion 12, 312 further includes a longitudinally extending tube or shroud 38, 338 defining a longitudinally extending opening or channel 40, 340 shaped to receive the hinge pin 22, 322. The hinge pin is disposed in the channel 40, 340 with the head engaging a bottom shoulder or rim formed in the shroud to fix the lower and upper portions 14, 314, 12, 312 together, but allow rotational and longitudinal movement therebetween. In this way, the hinge pin and shroud, or socket, act as a connector between the upper and lower portions. The container is inserted through the upper portion of the housing with a bottom end 102 of the container protruding from the upper portion and exposed to the user for actuation.

Referring to FIGS. 1A, 13-17, 57, 60 and 63A-B, the connector member 80, 380 otherwise referred to as a locking collar/member, includes a generally cylindrically shaped tube 82, 382 having an enlarged portion 84, 384 formed on one side thereof. The enlarged portion forms an interior cavity 86, 386 relative to a cylindrical boundary formed by the interior surface of the tube 82, 382. The upper and lower portions 12, 312, 14, 314 have an outer cylindrically shaped surface that is dimensioned to be received inside the tube portion 82, 382 of the connector member. An upper lip portion 24, 324 of the lower portion forms a friction fit with a bottom lip or rim 36, 336 of the upper portion (or vice versa) such that the upper and lower portions are releasably joined. The connector member maintains a connection between the upper and lower portions when in a locked position. The term "connected," or variations thereof, as used herein means that two or more members or components are coupled, whether directly or indirectly, for example with an intervening member or component. For example, it should be understood that the container is connected to the dispenser housing when it is connected to the indicator assembly, which in turn is connected to the dispenser housing. The term "fixedly connected," or variations thereof, means that one component connected to another is not meant to be disconnected during the normal operation of the device and without undue force, while "releasably connected," means that one component is meant to be disconnected during such normal operation and without undue force.

When the upper and lower portions are joined, the half-lugs 28, 328, 34, 334 form one or more guides that are disposed in a pair of horizontally or laterally, circumferentially formed slots 88, 388 formed in the connector member. The guides follow in the tracks defined by the slots 88, 388 to maintain the upper and lower portions in a locked position or configuration. A release opening 42, 342 is formed at one end of the slot 88 such that the slot 88 opens downwardly through the rim of the connector member. The slots can be numbered so as to correspond to the number of guides formed on the upper and lower portions. In the embodiment shown in FIGS. 60 and 63A-B, an annular rim portion extends around the lower perimeter of the connector member 388, with the opening 342 formed by a recess located interiorly of an our portion of the rim 343, as shown in FIGS. 63A-B.

The connector member further includes a pair of disengagement slots 44, 344 formed on opposite sides thereof. The slots are each configured with a ramped portion, extending both longitudinally and laterally around the locking collar 80, 380, and terminating at opposite ends in enlarged portions 46, 346, and longitudinally extending slot 48, 348. In one embodiment, the enlarged portions 46, 346 are configured as an upwardly, longitudinally extending slot, while the lower slot 48, 348 extends downwardly. The openings 44, 344, 46, 346, 48, 348 are shaped and dimensioned to receive the lugs 92, 292, 392 or followers of the retainer member, shown in FIGS. 1A, 57, 60 and 62A-B. The slots can be numbered so as to correspond to the number of lugs on the retainer member and the corresponding number of longitudinally extending slots formed on the upper member, i.e., one or more.

In one embodiment (see e.g., FIG. 15), the upper portion 46 is forms a small recess slot, or enlarged opening, while in another embodiment (see, e.g., FIGS. 8A-8E), the slot 46 extends vertically upwardly. The longer slot of FIGS. 8A-8E allow for the container to be further retracted into the cavity formed by the locking collar such that the valve stem is not exposed below the lower rim of the locking collar.

Figure 63A:
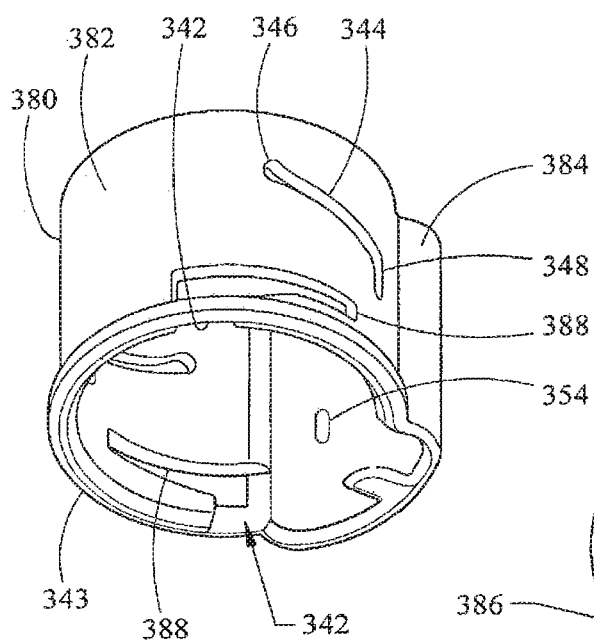
FIG. 63A is a bottom perspective view of one embodiment of a locking/connector member.
Figure 63B:
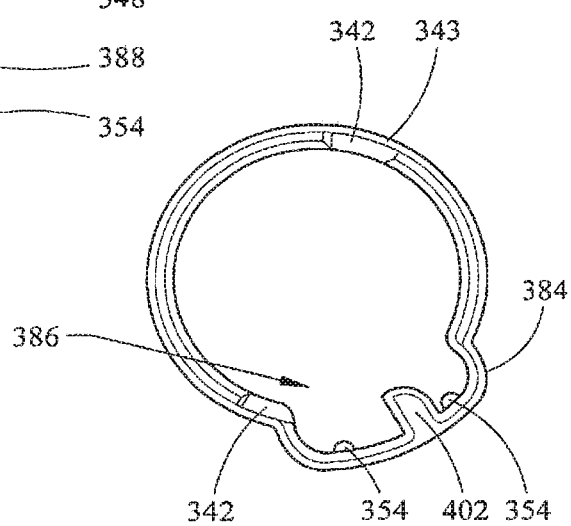
FIG. 63B is a bottom view of the locking/connector member shown in FIG. 63A.

Referring to FIGS. 63A-B, the connector/locking member 380 includes a locking member, or stop member 402, which extends radially inwardly from an interior of the enlarged portion 384 into the cavity 386, along a bottom edge portion of the enlarged portion.

Figure 61B:
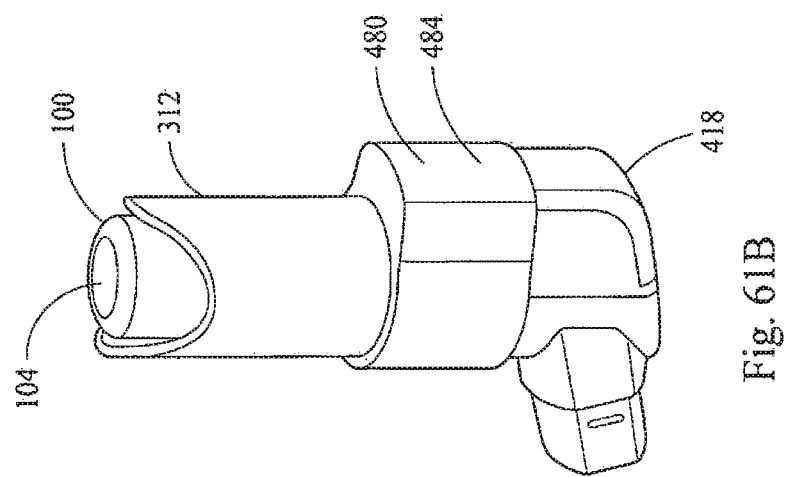
FIG. 61B is a perspective view of another embodiment of the dispensing device having a closed configuration locking/connector member.
Figure 61A:
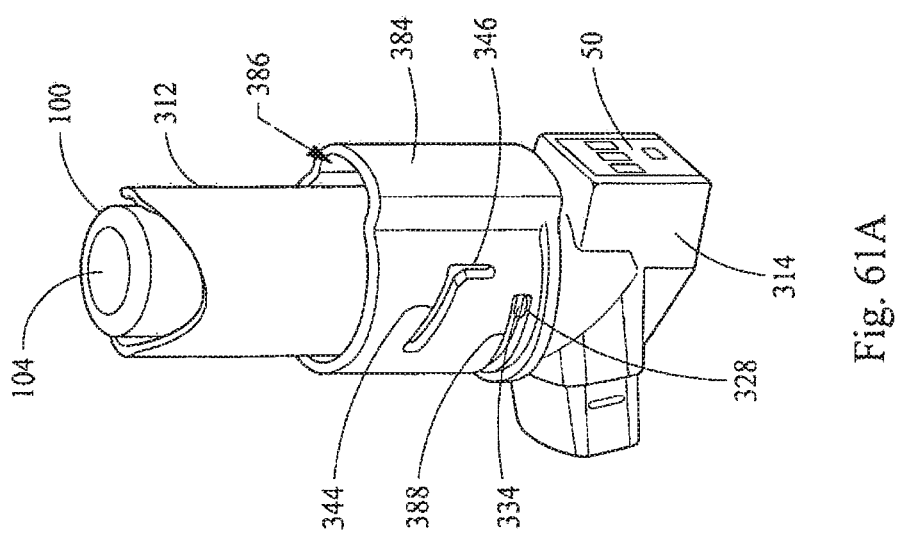
FIG. 61A is a perspective view of one embodiment of the dispensing device having an open configuration locking/connector member.

Referring to FIG. 61B, the top of the locking collar 480, and in particular enlarged portion 484, can be closed, so as to improve the aesthetics of the device, as well as to help reduce the likelihood of tampering and/or contamination. Likewise, the openings 388, 344, 346, 348 and 342 (see FIG. 61A) can all be formed on an interior surface of the collar 480. As such, it should be understood that the term "opening," "slot," etc., includes but does not require penetration through the entire thickness of a component, but rather is meant to include an undercut or recess formed in such a component. A bottom portion 418 of the lower portion 414 also can be curved so as to vary the aesthetics of the device.

Figure 57:
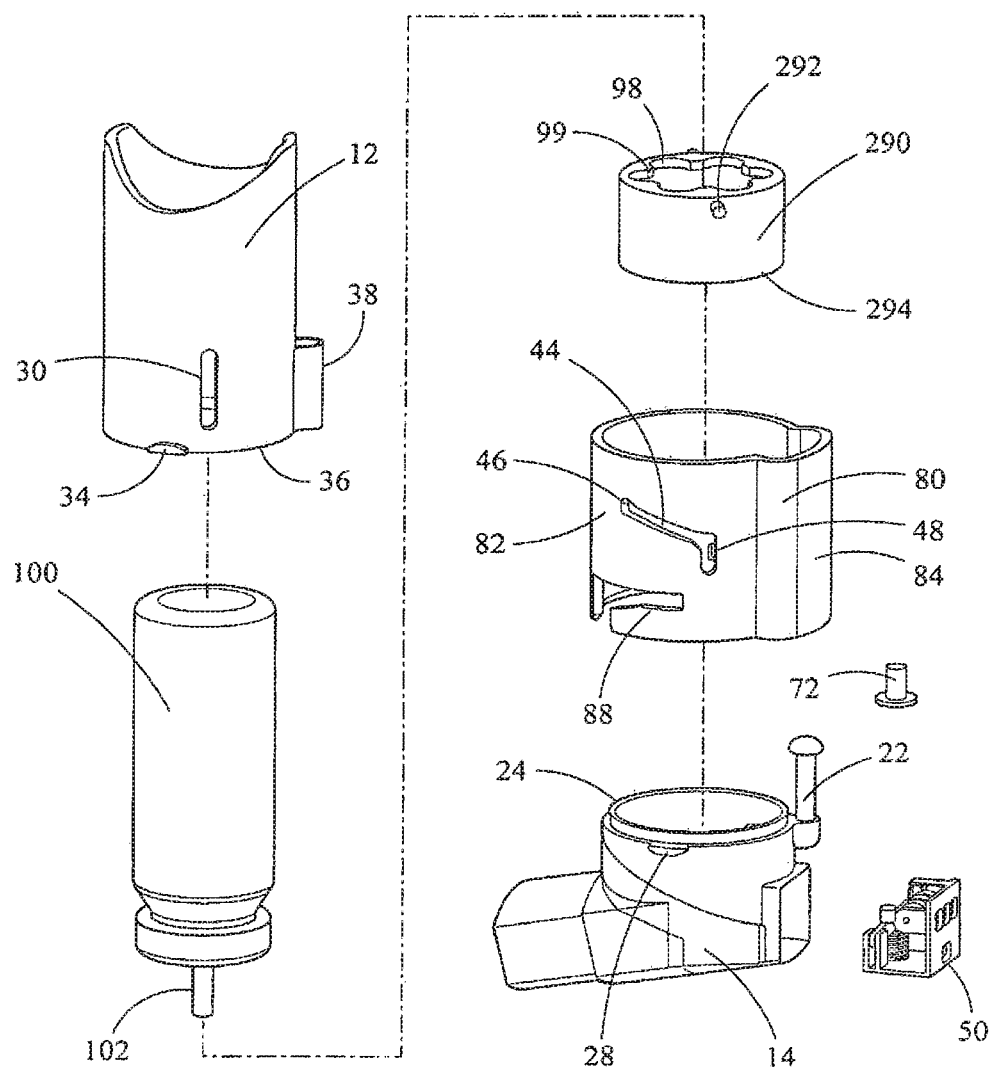
FIG. 57 shows an exploded view of the first embodiment of the dispensing device.
Figure 58:
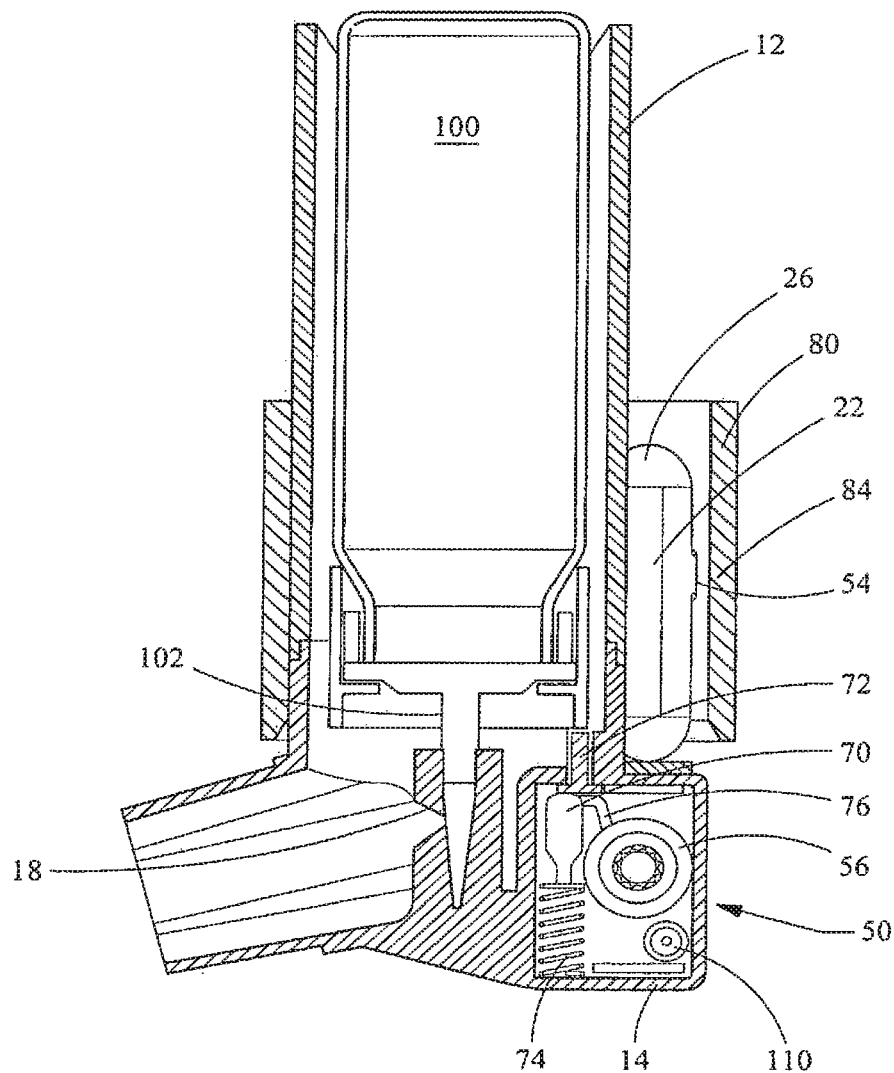
FIG. 58 shows a partial cross-sectional view of the indicating device shown in FIG. 57.
Figure 59:
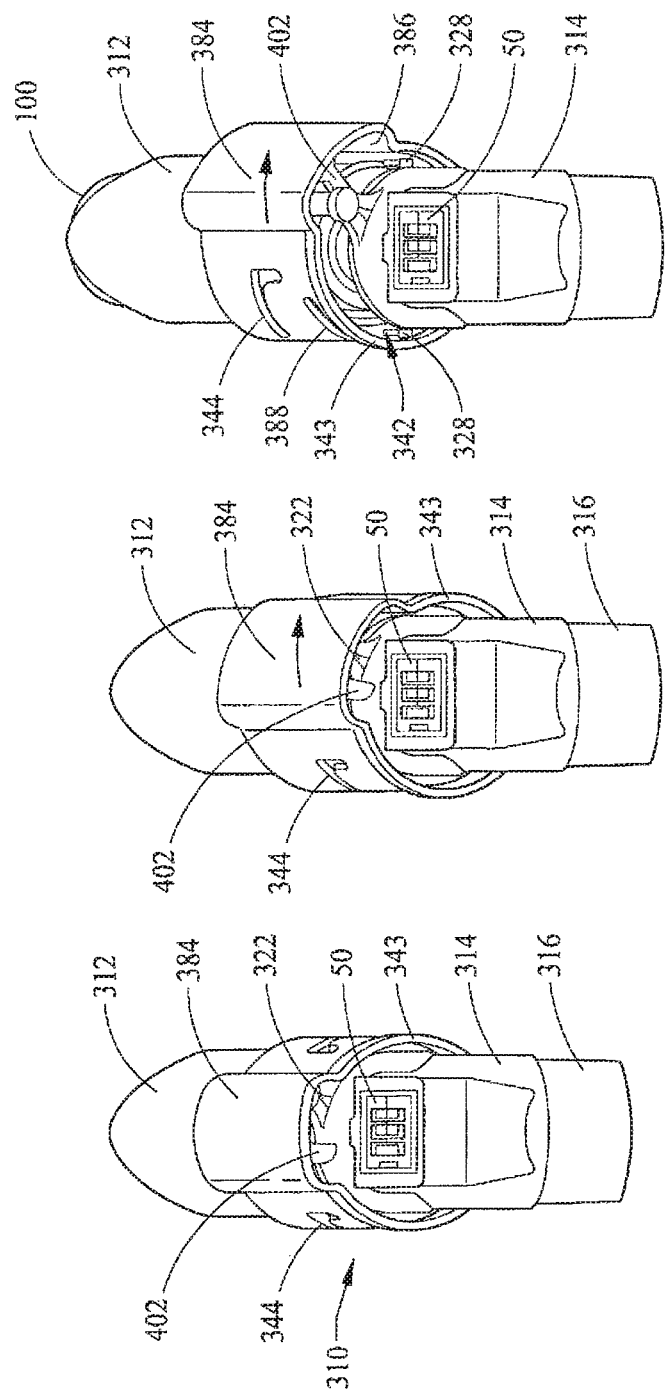
FIG. 59A is a bottom perspective view of a dispensing device in a ready-for-use position.
FIG. 59B shows the dispensing device of FIG. 59A moved between the ready-for-use and cleaning positions.
FIG. 59C shows the dispensing device of FIG. 59A in a cleaning position.
Figure 60:
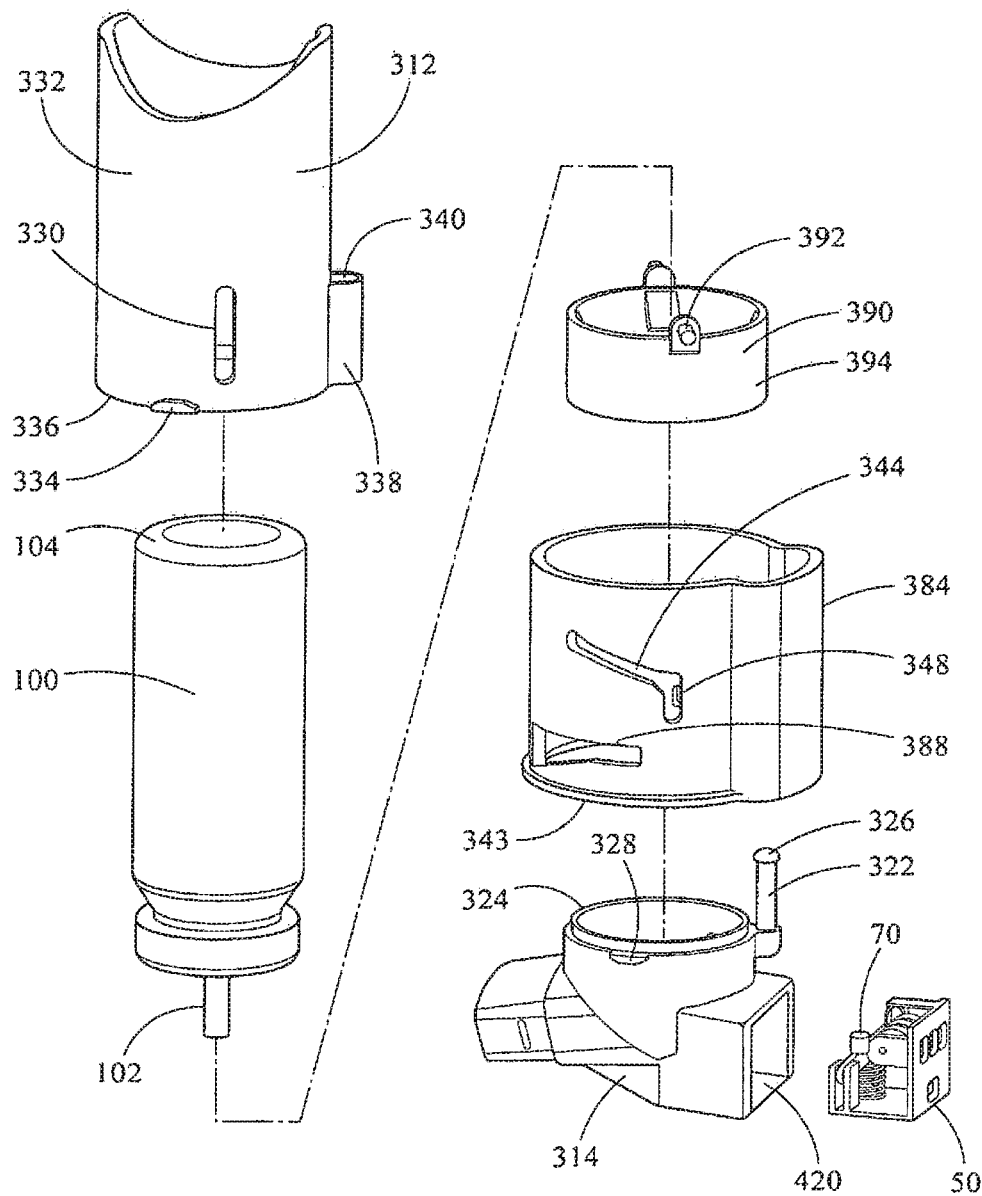
FIG. 60 is an exploded perspective view of another embodiment of the dispensing device.

Referring to FIGS. 1A, 24-28, 57, 60, 62A-B, the retainer member 92, 292, 392 includes a ring 94 or a collar 294, 394, a pair of flanges 96, 396 or supports extending longitudinally from the ring and a lug or pin 92, 292, 392, otherwise referred to as an engaging portion or follower, extending radially outward from each flange 96, 396, or as shown in FIG. 57 radially outward form the collar 294. The ring 94 and collar 294 have an inner scalloped rim 98 having a plurality of gripping portions 99 configured and dimensioned to engage a neck of the container 100. The ring or collar can be snapped onto the container so as to be fixedly connected thereto. The retainer member functions as and provides a connector member between the container and the dispenser housing.

Figure 62A:
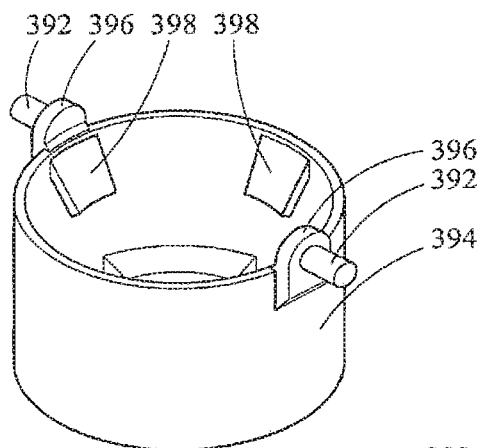
FIG. 62A is a top perspective view of one embodiment of a retainer member.
Figure 62B:
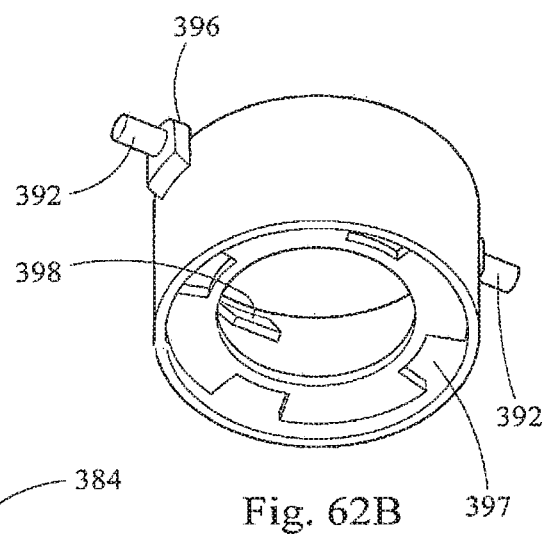
FIG. 62B is a bottom perspective view of the retainer member shown in FIG. 62A.

In the embodiment of FIGS. 62A-B, a plurality of tabs 398 engage the container, for example the ferrule portion thereof, with a snap fit, such that the collar 394 is fixedly connected to the container. Adjacent an opposite end of the collar 394, an annular ring 399, having a plurality of vent openings 397 positioned therein, defines a central opening through which the valve stem of the container extends. An end portion of the container is disposed between the ring 399 and the tabs 398. The diameter of the opening can be varied, for example such that the container can directly engage a portion of an indicating device, such as an actuation post 72. Alternatively, the post is engaged by the ring 399.

To assemble the device, the retainer 90, 190, 390, 390 is connected to the container 100. The upper portion 12, 312 is inserted through the locking collar 80, 380 such that the shroud 38, 338 is received in the cavity of the enlarged portion 84, 384. The lower portion 14, 314 is connected to the upper portion 12, 312, with the lugs 28, 328, 34, 334 mating and disposed through the release opening 42, 342, and into the circumferential slot 88, 388. The hinge pin 22, 322 is inserted through the channel 40, 340 to secure the upper member to the lower member, with the locking member 80, 380 disposed therearound. The support members 96, 396 of the retainer are flexed such that the lugs 92, 392, or guides, can be slid along longitudinally extending tracks 52 formed on an interior surface of the upper portion and thereafter be snap fitted through the longitudinal slots 30, 330 in the upper portion and the disengagement openings/slots 44, 344, 46, 346, 48, 348 of the connector member 80, 380.

In operation, and referring to FIGS. 8A-8E, 60 and 61A, the user operates the container 100 in the normal way, with the indicating device 50 providing an indication of the number of doses of medicament dispensed from or remaining in the container. During this sequence, the lugs 92, 392 of the retainer member simply move longitudinally in the longitudinal slot 30, 330 of the upper portion and the lower longitudinal slot 48, 348 of the disengagement slot formed in the locking collar. Referring to FIGS. 8A-E and 59A-C, when the support block 18, or other portion of the dispenser housing, requires cleaning, the user twists the locking collar member 80, 380 relative to the upper and lower portions 12, 312, 14, 314, or vice versa, with the combined guides 28, 328, 34, 334 moving within the circumferential slot 88, 388 and the shroud 38, 338 moving laterally within the cavity 86, 386 formed by the enlarged portion 84, 384. The shroud can be releasably fixed in a first, ready-for-use position and a second cleaning position by a pair of detents 54, 354 or protuberances formed on the interior surface of the enlarged portion (see, e.g., FIGS. 16, 63A-B), with the shroud held in one of the ready for use or ready for cleaning positions by the detents 54, 354. It should be understood that the hinge pin and shroud can be arranged on the other of the lower and upper portions.

As the connector member 80, 380 is rotated, the followers or lugs 92, 392 of the retainer member ride along the ramped portion 44, 344 of the slot, thereby forcing the container 100 upwardly relative to the lower portion and out of engagement with the support block 18. As the lugs 28, 328, 34, 334 are moved from a locked position in the slot 88, 388 to a release position over the release opening 42, 342, the user then can separate or move the lower portion from the upper portion in a longitudinal direction. While the guides 28, 328, 34, 334 are moved in the slot 88, 388, the container 100 and retaining ring 90, 292, 392, and in particular the followers 92, 292, 392, are moved longitudinally upward within the slots 30, 330, 44, 344 so as to disengage the valve stem from the support block. As the guide 28, 328 is moved through the release opening 42, 342, the lower portion 14, 314 is separated from the upper portion 12, 312. The lower portion 14, 314 is moved downwardly until the hinge pin head 26, 326 engages a stop portion formed at a bottom of the channel 40, 340 in the shroud. The lower portion 14, 314 then can be rotated about a longitudinal axis defined by the hinge pin 22, 322 so as to expose the support block for cleaning while maintaining a separation of the lower portion from the upper portion and the attached container. The device can be reassembled by following the reverse steps.

In this way, the container is maintained in connection with a specific indicating device such that the count of the device is not corrupted while at the same time allowing the container to be cleaned.

In another aspect, the container can be moved to a disengaged position, as shown in FIG. 8C, but with the lower portion and upper portion remaining in an engaged configuration, for example by way of the friction fit between the lip portion 24 and the rim 36. As such, the container cannot be inadvertently actuated, since the valve stem is not engaged with the support block, for example during transport. At the same time, the lower portion remains coupled to the upper portion such that the valve stem is not exposed. The dispenser housing can also be configured with a detent, or an additional slot, that maintains the position of the container in the disengaged position while the upper and lower portions remain engaged.

In one embodiment, one or both of slot 46, 346 or the upper portion of slot 30, 330 is tapered or narrowed so as to frictionally engage the followers 92 and maintain a disengaged position of the container relative to the lower portion and support block such that the container does not inadvertently slide back down the ramped slot 44 and become engaged or inadvertently actuated.

Referring to the embodiment shown in FIGS. 59A-C, as the locking collar 380 is rotated, the stop or locking member 402 passes beneath a bottom portion of the hinge pin 322. As the upper and lower portions 312, 314 are then separated (see, FIG. 59C), the stop member 402 is moved relative to the pin 322, such that the pin is disposed between the stop/locking member 402 and a shoulder portion of the enlarged portion 384. In this way, the stop/locking member 402 engages the pin 322, and prevents rotation of the collar 380 while the device is in the open, cleaning position. This prevents the user from attempting to rotate the collar 380 while the upper and lower portions 312, 314 are separated or spaced apart in the longitudinal direction.

In another embodiment, shown in FIGS. 29-53, the dispensing device includes a lower, mouthpiece portion 114, an upper, chimney portion 112 and a retainer member 190. As described above with respect to the first embodiment, an indicating device 50 is disposed and secured in the lower portion 114, which also includes a mouthpiece 16 and support block 18. A lip portion or rim 124 is formed around the upper circumferential rim of the lower portion and engages the lower circumferential rim 136 of the upper portion with a friction fit. One of the lower portion and upper portion includes a pair of spaced apart lugs 134, while the other of the upper and lower portions includes a hinge pin 122 secured to the lugs so as to form a pivotable connection between the upper and lower portions. The hinge pin can be formed integrally with one or both of the upper and lower portions, or can be formed as a separate member, and can be engaged with a socket or lugs formed on the other of the upper and lower portions. The upper and lower portions alternatively can be formed integrally with a living hinge connecting those portions. The hinge pin forms a connector between the upper and lower portion. The upper portion further includes a pair of loops or guides 138 extending radially inward from an interior surface thereof, as shown in FIG. 51.

The retainer 190 includes a pair of elongated arms 196, each having a hook or engaging portion 192 formed at a terminal end thereof. The retainer also includes a ring portion 194 with a rim 98 and gripping members 99 as described above. The retainer functions as and forms a connector between the container and the dispenser housing.

To assemble the device, the container 100 is connected to the retainer 190, and the upper and lower portions are pivotally engaged by way of the hinge pin 122. The retainer 190 and container are then inserted with the arms 196 extending through the guides 138 of the upper portion and with the engaging portion 192 bottoming out on, or engaging, the guides 138 when the container is in a disengaged position. It should be understood that the steps of the various installation methods can be rearranged as deemed suitable.

In operation, the user pulls the container 100 upwardly in a longitudinally direction until the engagement portions 192 on the ends of the arms engage a lower surface of the guides 138. In this position, the valve stem 102 is disengaged from the support block 18 of the lower portion. The user then rotates the container and upper portion about the hinge axis relative to the lower portion to expose the support block to the user for cleaning. The device can be reassembled following the reverse steps.

The term "longitudinal" as used herein is intended to indicate the direction of the reciprocal movement of the container relative to the housing. The terms "top," "bottom," "upwardly" and "downwardly" are intended to indicate directions when viewing the inhalation devices as shown in the Figures, but with the understanding that the container is inverted such that the top surface thereof is located adjacent the bottom of the housing and vice versa.

The container 100 is formed as a cylindrical canister having a hub disposed on a top surface thereof. The container also has a shoulder and a neck portion. The valve stem 102 extends longitudinally from the hub. The valve stem extends coaxially from the canister and is biased outwardly therefrom by a spring (not shown) mounted within the canister. The container 100 is mounted in the dispenser housing by press fitting the valve stem in the well of the support block 18, which defines an "engaged" position of the container. The container is in a "disengaged" position when the valve stem 102 is removed from the well of the support block 18.

It should be understood that the container can be configured in a variety of shapes and sizes, and that the substance contained therein can be released by any number of valve systems that are well known in the art. It should also be understood that the valve system can be actuated by a variety of actuators, including, but not limited to, various pumps, levers, actuator boots, buttons and the like. In such embodiments, the valve system can be actuated by an actuator moveable relative to the container and housing such that the container remains stationary relative to the housing.

In a preferred embodiment, the container 100 is filled with a substance which is dispensed therefrom in specific metered doses by depressing or moving the valve stem 110 from an extended closed position to a depressed open position, which in turn opens the value or value system. Preferably the substance is a medicament, although it should be understood that the container should be used to hold a variety of non-medicinal substances, including, but not limited to, various liquids, foams or aerosols. A single metered dose is dispensed from the container by each reciprocal, longitudinal movement of the valve stem and attendant opening and closing of the valve.

In operation, the opening of the valve stem and valve is effected by moving the container 100 reciprocally within the housing 10 along a longitudinal axis, defined by the valve stem and the reciprocal movement of the container, by depressing the exposed bottom end 104 of the canister relative to the housing 10 so as to move the valve stem 110 to the open position as it is supported within the well by the support block. Alternatively, an actuator can be moved to open the valve system of the container, which can remain stationary with respect to a supporting housing, a cap and/or an indicating device mounted thereto. For example, the actuator can be attached to the end of the container in the form of a pump device or the like.

As the valve stem is moved to the open position, the container dispenses a metered dose of the substance in aerosol form through the well and orifice and into the exhaust port. The substance in aerosol form is then transmitted to the user through the exhaust port of the mouthpiece by way of either a self-generated or assisted airflow. Alternatively, metered doses of liquids and the like can be dispensed from the container.

In other delivery systems, the housing and holder for the container are attached to a component having a chamber with an output end. Examples of these kinds of delivery systems are shown for example in U.S. Pat. No. 5,012,803, issued May 7, 1991, and U.S. Pat. No. 4,460,412, issued Sep. 11, 1984, the entire disclosures of which are hereby incorporated herein by reference. (No license, expressed or implied, is intended to be granted to any patent by reason of the incorporation by reference herein.) In these kinds of delivery systems, the component having the chamber can be adapted to receive the mouthpiece of the housing, or it can be integrally connected with a holder supporting the container. In either embodiment, the metered dose of substance, preferably a medicament, in aerosol is first dispensed from the container into the chamber, and thereafter inhaled by the user. Other dispensing devices are also shown in U.S. application Ser. No. 11/334,940, filed Jan. 19, 2006 and entitled Dispensing Device, the entire disclosure of which is hereby incorporated herein by reference.

In a preferred embodiment, the container 100 is intended to dispense a predetermined number of metered doses of substance. For example, conventional inhaler containers typically hold on the order of 100 to 200 metered doses. In operation, it is important that the user be aware of the number of metered doses remaining in the container such that the user is not caught unaware with an empty canister when in need of the substance, such as a medicament. It should be understood, however, that the dispenser housing, with its upper and lower portions, can be used without an indicating device, for example to ensure that a particular container is used with a specifically suited dispenser housing.

Now referring to FIGS. 1A, 3, 29, 31 and 54A-58, the indicating device 50, or indicator assembly, is disposed in the lower portion 14, 114. The indicator assembly can take many forms, as disclosed for example and without limitation in U.S. Pat. Nos. 6,142,339, 6,161,724, 6,435,372 and 6,561,384, the entire disclosures of which are hereby incorporated herein by reference. The indicator assembly can include a single indicator member, or a plurality of (i.e., more than one) indicator members, shown for example as three co-axially mounted indicator members 56 in the various embodiments of FIGS. 54A-58. In addition, the indicator assembly can be configured as a mechanical device or an electrical device, or a combination thereof, and can include without limitation various analog and digital readouts and indicia.

Referring to FIGS. 54A-58, an actuator includes an actuator arm 70 having a first end pivotally connected to a housing. A post member or plunger 72 is longitudinally moveable and engages the actuator arm at a distance from the hinge axis of the arm. In one embodiment, the post member is connected to the actuator arm, and in one embodiment is integrally formed therewith. The plunger is moveably supported in the housing along an axis parallel to the longitudinal axis defined by the reciprocal movement of the container within the housing. A spring 74 is disposed between the arm 70 and the housing. In various embodiments, the spring can be configured as a leaf spring 73 or a coil, compression spring or a cantilever spring 71, which engages a ramped surface on the arm 70. An end portion of the actuator arm with the ramped surface slides along and biases or bends the resilient cantilever spring. In any of these embodiments, the spring 74 biases the actuator arm and ultimately the plunger upwardly against the top surface of the canister, or against a mounting portion secured thereto. It should be understood that torsion (e.g., acting at the hinge/pivot axis) and tension springs, and the like, would also work to bias the actuator member upwardly into engagement with the container. A stop member 424 limits the upward travel of the actuator member. The springs can be made of metal or plastic.

In operation, the container is moved longitudinally within the housing so as to depress the valve stem to the open position and thereby open the valve as explained above. As the container is moved downwardly within the housing, the actuator arm 70 is moved longitudinally downward as it is pivoted about its hinge axis. When the container is released by the user, the spring (not shown) within the container biases the container upwardly within the housing along the longitudinal axis such that the valve stem 102 is moved to the closed position within the container so as to close the valve, while the spring 74 biases the actuator arm upwardly. As the actuator is reciprocally moved, an end 76 thereof opposite the pivot axis is configured with a ratchet arm, which selectively engages a ratchet gear 78, which in turn operably moves one or more the indicator members 56 upon a predetermined number of reciprocal movements.

The indicator members 56 are provided with indicia that are visible through one or more viewing windows formed in the lower portion. The indicia indicate to the user the number of doses that remain in or have been dispensed from the container. In one embodiment, the indicia take the form of a color code, where, for example, a portion of the wheel is colored green to indicate the starting full position, a portion is colored yellow to indicate a medium fullness and a portion is colored red to indicate that the container is empty. Obviously, other colors, shading or alpha-numerical indicia can be provided on the indicator wheel to indicate the relative fullness or emptiness of the container.

In one embodiment, the indicator assembly includes three indicator members 56 coaxially mounted on an axle and rotatable thereabout. Each of the indicator members is configured as an indicator wheel having a circumferential skirt with an outer circumferential surface on which indicia (shown as numbers) are applied. In this embodiment, the ratchet gear 78 is coaxially mounted with the indicator wheel. The ratchet gear 78 includes a plurality of teeth formed around its periphery. In one embodiment, the ratchet gear is integrally molded with the indicator wheel, although it should be understood that the gear and wheel can be made separately and thereafter attached one to the other by welding, adhesive and the like.

In one embodiment, the first indicator member includes a resilient advancement member 58 that overlies ratchet gear teeth formed on the second indicator member. Likewise, the second indicator member includes an advancement member 58 that overlies ratchet gear teeth formed on the third indicator member. It should be understood by one of skill in the art that one or more indicator members may be used to provide an indication of dosages used or available, and that the three indicator members shown in the Figures is meant to be illustrative, rather than limiting. In addition, it should be understood that a plurality of indicator members refers to any number of indicator members greater than one.

Referring to FIGS. 54A-58, an indicator housing 38 is shown as having a pair of engagement members 62 formed integrally with the housing and including ramped surfaces. A plurality of non-return members 64 extend from the housing and selectively engage the ratchet gear(s) to ensure unidirectional rotation of the indicator member(s). Although the engagement members and non-return members are shown as being formed in or extending from a module housing, one of skill in the art should understand that those members or equivalent features could also be formed in or connected to the dispenser housing or actuator boot that supports the container or disposed on or connected to the container itself.

In operation, the container is moved longitudinally within the housing 10 so as to depress the valve stem 102 to the open position so as to open the valve as explained above. As the container is reciprocally moved within the housing, the actuator arm 70, or pawl portion 76 thereof, engages the ratchet gear 78 secured to the first indicator member and rotates the first indicator member a predetermined angular or incremented amount corresponding to the pitch of the teeth disposed around the periphery of the ratchet gear. A stop member 424 is disposed over the pawl portion 76 so as to limit the rebound of the actuator arm 70.

The reciprocal movement of the container relative to the housing is repeated until the first indicator member 56, and its ratchet gear 78, are rotated one complete revolution. The predetermined number of reciprocal movements required to advance the first indicator member one revolution is equal to the number of teeth disposed about the periphery of the ratchet gear 78. As the first indicator member is rotated by successive movements of the container relative to the housing, the advancement member 58 of the first indicator member is brought into selective engagement with the engagement member 62, configured with the ramped surface formed in the housing. In particular, the engagement member 62 biases a tooth portion of the advancement member 58 into engagement with one of the teeth of the ratchet gear 78 on the second indicator member.

As the first indicator member is further rotated by successive movements of the container relative to the housing, whether it be the dispenser housing for the container or the module housing described below, the advancement member 58 engages one of the teeth on the ratchet gear 78 of the adjacent (i.e., second) indicator member and advances the indicator member a predetermined incremental angular amount corresponding to the pitch of the ratchet gear teeth. The term incremental is meant to refer to the angular amount the indicator member is moved by the advancement of one actuation, which corresponds to the movement of one tooth, regardless of whether the indicating device is indicating the number of doses left (e.g., counting down) or indicating the number of doses administered (e.g., counting up).

As the resilient advancement member 58 clears the engagement member 62, it springs away from the ratchet gear such that further advancements of the first indicator member do not effect a rotation of the second indicator member until the first indicator member completes yet another cycle so as to again bring the advancement member into engagement with the next tooth of the second indicator member ratchet gear, and so on. The second indicator member with its advancement member 58 similarly interacts with a second engagement member 62 overlying ratchet teeth of the third indicator member so as to selectively engage and advance the third indicator member a predetermined incremental amount for each complete rotation of the second indicator member. It should be understood that more indicator members could be similarly assembled to provide an incremental indicating device.

A secondary or warning indicator member 110 is rotatably supported in the dispenser housing adjacent the indicator members about an axis parallel to and spaced apart from the axis of the indicator members 56. The warning indicator 110 has an outer circumferential surface with warning dosage indicia applied thereto. Preferably, the warning dosage indicia takes the form of a color coding, for example a portion or zone of the surface is green, while another portion or zone is red. Preferably a plurality of zones is used, for example and without limitation two zones of green and red respectively, or three zones of green, yellow and red. Alternatively, alphanumeric characters, text messages etc. as herein described can be used as indicia. It should be understood that a surface of the indicator member perpendicular to the axis of rotation also can be configured with the indicia. The surface of the indicator member is visible through a viewing window formed in the lower portion of the dispenser housing.

The second indicator member 110 further includes at least one driven member 306, and preferably a plurality of driven members, configured in one embodiment as a teeth extending radially outward from the second indicator member on one side of the circumferential indicia surface. Taking into account the spacing between the axes of rotation for the primary indicator members 56 and the secondary indicator member 110, a drive member coupled to one of the indicator members and the driven members are configured and have sufficient lengths so as to mesh after a predetermined number of rotations of the first indicator member 56 configured with the drive member. The second indicator member 110 is also provided with a plurality of ratchet teeth formed circumferentially around the axis of rotation on the side of the indicator member opposite the drive member. A non-return member extends from the dispenser housing or module housing and successively, selectively engages one or more of the ratchet teeth so as to allow the second indicator member 110 to rotate in only one direction. Various embodiments incorporating a warning indicator are further disclosed in U.S. patent application Ser. No. 10/968,815, filed Oct. 18, 2004 and entitled Indicating Device With Warning Dosage Indicator, the entire disclosure of which is hereby incorporated herein by reference.

In a preferred embodiment of the dispenser, the indicator assembly is arranged in an indicator module. The indicator module is shaped to be received within the lower portion 14, 114 of the dispenser housing where it is disposed around a portion of the support block 18. In particular, the support block is spaced apart from the wall of the dispenser housing, otherwise referred to as the actuator boot, so as to form a donut-shaped socket in the bottom of the housing. The module includes a module housing 60 having an inner concave surface that is shaped to mate with an outer convex surface of the cylindrical support block and an outer convex surface that is shaped to mate with the inner concave surface of the housing which is also generally cylindrical. In this way, the module housing is shaped to be received within the socket formed around the support block. Preferably, the module housing has a semicircular shape and fits around a portion of the support block opposite the orifice opening so as to not interfere with the dispensing of the medicament, or the airflow transmitting the medicament to the patient. In this way, the module is maintained rearwardly of the midpoint of the support block. One of skill in the art should understand, however, that the module, or module housing, can be configured in any number of different sizes and shapes so as to be accommodated in a variety of housings or cap assemblies, with or without support blocks and the like. The module housing can be made of a single piece, or from two or more pieces joined to form the housing.

It should be understood, however, that the module can be secured within the housing by any number of conventional means, including the use of fasteners or adhesive. Alternatively, the module can simply be press fit into the socket formed between the support block and housing wall. In one embodiment, the module is inserted through an opening 420 in the lower portion, wherein a face member 422 of the housing is secured to the lower portion, for example with a snap fit, adhesive, friction fit, or other known connection devices. The post member 72 can thereafter be connected to the actuator arm 70

In various embodiments, as explained above, the indicia are applied to a circumferential surface of the indicator wheel, for example in the form of numbers ranging from 0 to 9, with the ratchet gear on the indicator member having 10 teeth. In operation, it should be understood that the three, or more or less, indicator members can be preset to the maximum number of dosages contained within the container, with the indicia, or in this case numbers, arranged about the periphery of the indicator wheel, such that successive, sequential actuations of the container cause the indicator members to count down.

Alternatively, the indicator members are assembled such that the zero (0) of each indicator member is displayed in the viewing window to the user. The container is then actuated by the user such that the first indicator member rotates within the housing to sequentially display the number of doses that have been dispensed from 1 to 9. Upon the tenth actuation, the indicator member completes a single revolution, by virtue of the ten teeth preferably formed about the ratchet gear which correspond to the predetermined number of actuations, and causes the second indicator member to advance one number from 0 to 1 as the first indicator member again displays a 0 such that the two members together indicate that 10 dosages have been dispensed. The first indicator member is again rotated by successive actuations until another single rotation is completed to further rotate the second indicator to reveal the 2, so as to indicate that 20 dosages have been dispensed. Upon a complete rotation of the second indicator member, corresponding to 100 actuations, the third indicator member is advanced to reveal a 1 in the viewing window with the first and second indicator members revealing a 0, and so on.

Although the indicator assembly embodiments of FIGS. 54A-58, for example, are shown as being mounted in the indicator module, one of skill in the art should understand that the assembly, including the axle, indicator members, ratchet gears, actuator member and spring could be mounted directly in the dispenser housing or actuator boot that supports the container. Similarly, the engagement member, or members, and non-return member, or members, could be formed in the dispenser housing that supports the container, otherwise referred to as the actuator boot.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A dispenser for use with a container for dispensing dosages of a substance from the container, the dispenser comprising:
    a dispenser housing comprising:
        a lower portion having a nonremovable support block and a first outermost surface, wherein said support block comprises a well shaped to receive a valve stem of the container;
        a tubular upper portion directly connected to the lower portion and defining a cavity shaped to receive the container, wherein said tubular upper portion and said cavity extend in a longitudinal direction, said tubular upper portion having a second outermost surface, wherein said first and second outermost surfaces are flush;
    a tubular housing comprising an inner surface circumferentially surrounding said second outermost surface of at least a portion of said tubular upper portion, wherein said tubular housing has a third outermost surface, wherein said third outermost surface of said tubular housing is spaced radially outwardly from said first outermost surface of said lower portion and said second outermost surface of said upper portion, wherein said tubular housing is connected to said dispenser housing, and wherein said tubular housing is non-movable relative to said tubular upper portion in said longitudinal direction; and
    an indicating device connected to said dispenser housing.

2. The dispenser of claim 1 wherein said indicating device is disposed interiorly in said dispenser housing.

3. The dispenser of claim 2 wherein said indicating device is disposed in said lower portion of said dispenser housing adjacent said support block.

4. The dispenser of claim 1 wherein said tubular housing circumferentially surrounds at least a portion of the first outermost surface of said lower portion.

5. The dispenser of claim 1 wherein said tubular housing is moveable relative to said dispenser housing from a locked configuration to an unlocked configuration.

6. The dispenser of claim 5 wherein said upper and lower portions are non-moveably connected when said tubular housing is in said locked configuration, and wherein said upper and lower portions are moveably connected when said tubular housing is in said unlocked configuration.

7. The dispenser of claim 6 wherein said tubular housing comprises a first slot and said upper portion comprises a second slot aligned with said first slot, and further comprising a retainer having a follower moveable in said first and second slots, wherein said retainer is adapted to be coupled to and in direct contact with said container.

8. The dispenser of claim 7 wherein at least a portion of said first slot is ramped along a longitudinal direction.

9. The dispenser of claim 7, wherein said retainer is moveably connected to said upper portion.

10. The dispenser of claim 9 wherein said retainer comprises a retainer ring adapted to be disposed around a portion of said container and an engaging portion extending from said retainer ring and moveably engaging said upper portion.

11. The dispenser of claim 1, wherein said tubular housing comprises an enlarged portion formed on one side thereof.

12. The dispenser of claim 1 wherein said indicating device comprises an indicator comprising dosage indicia.

13. The dispenser of claim 1 further comprising said container disposed in said cavity.

14. The dispenser of claim 13 wherein said container is moveable relative to said upper portion and said tubular housing.

15. The dispenser of claim 13 where said container holds a medicament.

16. The dispenser of claim 1, wherein said lower portion and said upper portion are pivotally connected and moveable about a pivot axis.

17. The dispenser of claim 1 wherein said indicating device is separate from said dispenser housing.

18. A dispenser for dispensing dosages of a substance, the dispenser comprising:
    a dispenser housing comprising:
        a lower portion having a nonremovable support block and a first outermost surface;
        a tubular upper portion directly connected to the lower portion and defining a cavity shaped to receive a container, wherein said tubular upper portion and said cavity extend in a longitudinal direction, said tubular upper portion having a second outermost surface, wherein said first and second outermost surfaces are flush;
    a tubular housing comprising an inner surface circumferentially surrounding said second outermost surface of at least a portion of said tubular upper portion, wherein said tubular housing has a third outermost surface, wherein said third outermost surface of said tubular housing is spaced radially outwardly from said first outermost surface of said lower portion and said second outermost surface of said upper portion, wherein said tubular housing is connected to said dispenser housing, and wherein said tubular housing is non-movable relative to said tubular upper portion in said longitudinal direction;
    an indicating device connected to said dispenser housing; and
    wherein said container is disposed in said cavity and has an end portion comprising a valve stem disposed in said support block.

19. The dispenser of claim 18 wherein said indicating device is disposed interiorly in said dispenser housing.

20. The dispenser of claim 19 wherein said indicating device is disposed in said lower portion of said dispenser housing adjacent said support block.

21. The dispenser of claim 18 wherein said tubular housing circumferentially surrounds at least a portion of the first outermost surface of said lower portion.

22. The dispenser of claim 18 wherein said tubular housing is moveable relative to said dispenser housing from a locked configuration to an unlocked configuration.

23. The dispenser of claim 22 wherein said upper and lower portions are non-moveably connected when said tubular housing is in said locked configuration, and wherein said upper and lower portions are moveably connected when said tubular housing is in said unlocked configuration.

24. The dispenser of claim 18, wherein said tubular housing comprises an enlarged portion formed on one side thereof.

25. The dispenser of claim 18 wherein said indicating device comprises an indicator comprising dosage indicia.

26. The dispenser of claim 18 wherein said container is moveable relative to said upper portion and said tubular housing.

27. The dispenser of claim 18 where said container holds a medicament.

28. The dispenser of claim 18 wherein said indicating device is separate from said dispenser housing.

\* \* \* \* \*